US008685703B2

(12) United States Patent
Yukawa et al.

(10) Patent No.: US 8,685,703 B2
(45) Date of Patent: Apr. 1, 2014

(54) CORYNEFORM BACTERIUM TRANSFORMANT HAVING IMPROVED D-XYLOSE-UTILIZING ABILITY

(75) Inventors: Hideaki Yukawa, Kyoto (JP); Masayuki Inui, Kyoto (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 215 days.

(21) Appl. No.: 12/995,774

(22) PCT Filed: Jun. 10, 2009

(86) PCT No.: PCT/JP2009/060637
§ 371 (c)(1),
(2), (4) Date: Jan. 18, 2011

(87) PCT Pub. No.: WO2009/154122
PCT Pub. Date: Dec. 23, 2009

(65) Prior Publication Data
US 2011/0117612 A1 May 19, 2011

(30) Foreign Application Priority Data
Jun. 17, 2008 (JP) ................. 2008-157409

(51) Int. Cl.
C12N 1/20 (2006.01)
C12N 15/00 (2006.01)
C12P 1/00 (2006.01)
C12P 13/04 (2006.01)
C12P 7/56 (2006.01)
C12P 7/54 (2006.01)
C12P 7/46 (2006.01)
C12P 7/06 (2006.01)
C07K 1/00 (2006.01)
C07H 21/04 (2006.01)

(52) U.S. Cl.
USPC ....... 435/252.32; 435/41; 435/69.1; 435/106; 435/139; 435/140; 435/145; 435/161; 435/320.1; 530/350; 536/23.7

(58) Field of Classification Search
None
See application file for complete search history.

(56) References Cited

U.S. PATENT DOCUMENTS

2004/0072312 A1 4/2004 Yukawa
2007/0087423 A1 4/2007 Murakami et al.

FOREIGN PATENT DOCUMENTS

| JP | 2002-338596 | 11/2002 |
|---|---|---|
| JP | 2002-338956 | 11/2002 |
| JP | 2004-089029 | 3/2004 |
| JP | 2008-517583 | 5/2008 |
| JP | 2009-050236 | 3/2009 |
| WO | 01/96573 | 12/2001 |
| WO | 2005/010182 | 2/2005 |
| WO | 2006/043730 | 4/2006 |

OTHER PUBLICATIONS

International Search Report issued Jul. 7, 2009 in International (PCT) Application No. PCT/JP2009/060637.
H. Kawaguchi et al., "Engineering of a Xylose Metabolic Pathway in *Corynebacterium glutamicum*", Applied and Environmental Microbiology, vol. 72, No. 5, pp. 3418-3428, May 2006.
I. Sa-Nogueira et al., "Cloning, Functional Analysis, and Transcriptional Regulation of the *Bacillus subtilis* araE Gene Involved in L-Arabinose Utilization", Journal of Bacteriology, vol. 179, No. 24, pp. 7705-7711, Dec. 1997.
International Preliminary Report on Patentability and English translation of the Written Opinion issued Jan. 11, 2011 in corresponding International Application No. PCT/JP2009/060637.
Extended European Search Report mailed Jun. 12, 2012, in corresponding EP Application No. 09 76 6570.7.
Kawaguchi H. et al., Identification and functional analysis of the gene cluster for L-arabinose utilization in *Corynebacterium glutamicum*. Appl Environ Microbiol. Jun. 2009; 75(11):3419-3429.
Gopinath V. et al., *Corynebacterium glutamicum* as a potent biocatalyst for the bioconversion of pentose sugars to value-added products. Appl Microbiol Biotechnol. Jan. 2012; 93(1):95-106.
Sasaki, M. et al., Engineering of pentose transport in *Corynebacterium glutamicum* to improve simultaneous utilization of mixed sugars. Appl Microbiol Biotechnol. Nov. 2009; 85(1):105-115.
Kawaguchi H. et al., Engineering of an L-arabinose metabolic pathway in *Corynebacterium glutamicum*. Appl Microbiol Biotechnol. Jan. 2008; 77(5):1053-1062.

*Primary Examiner* — Iqbal H Chowdhury
(74) *Attorney, Agent, or Firm* — Wenderoth, Lind & Ponack, L.L.P.

(57) ABSTRACT

A coryneform bacterium transformant prepared by transferring an exogenous gene which encodes a protein having a sugar transporter function into a coryneform bacterium capable of utilizing D-xylose.

8 Claims, 7 Drawing Sheets

CORYNEFORM BACTERIUM TRANSFORMANT HAVING IMPROVED D-XYLOSE-UTILIZING ABILITY

This application is a U.S. national stage of International Application No. PCT/JP2009/060637 filed Jun. 10, 2009.

TECHNICAL FIELD

The present invention relates to a D-xylose-utilizing technology. In more detail, the present invention relates to a coryneform bacterium transformant created by genetic modification for an improved D-xylose-utilizing ability, and relates to an effective organic-compound-producing technology using the same.

BACKGROUND ART

Cellulosic biomass is useful as a raw material for producing various kinds of organic acid compounds, ethanol, or the like by a biological method. The usefulness of cellulosic biomass is attributable to its availability. Unlike sugar-based biomass, such as cone starch and sugar, cellulosic biomass is readily available in various forms, such as agricultural waste or woody waste, at low cost, and therefore is not supposed to be any future obstacle to securing food resources. Cellulosic biomass comprises about 35 to 45% by mass of cellulose, about 30 to 40% by mass of hemicellulose, about 10% by mass of lignin, and about 10% by mass of other ingredients. Cellulose is a polymer of glucose (a hexose). Meanwhile, hemicellulose mainly consists of pentoses, such as xylose and arabinose.

The hemicellulose of cellulosic biomass, such as corn stover, wheat straw, rice straw, and bagasse, mainly consists of D-xylose. Therefore, for effective utilization of cellulosic biomass, it is imperative to establish a technology in which D-xylose is effectively utilized by a biological method.

In a cellulosic biomass utilizing technology, it is necessary to firstly saccharify the raw material into monosaccharides, such as hexose and pentose, and for a reason of process design, these monosaccharides coexist in a culture medium for producing organic compounds. Usually, in such a case, so-called "glucose repression" of a pentose by a hexose occurs. Glucose repression, which makes it impossible to utilize a hexose and a pentose in parallel and simultaneously, is a factor complicating process design and operation control, and is a hindrance to establishing a technology for industrial and effective utilization of biomass. Improvement in this regard is also desired.

Many microorganisms which utilize glucose, a kind of hexose, to produce various kinds of organic compounds by fermentation are well known, and some microorganisms which utilize D-xylose, a kind of pentose, to produce ethanol etc. are also known.

Patent Literature 1 and Non Patent Literature 1 disclose a technology in which wild-type *Saccharomyces cerevisiae* incapable of utilizing D-xylose is provided with a D-xylose-utilizing ability by transferring 3 genes, that is, a xylose reductase gene and a xylitol dehydrogenase gene both from *Pichia stipitis*, and a xylulokinase gene from *Saccharomyces cerevisiae* via plasmids; and a D-xylose-utilizing technology with use of the obtained *Saccharomyces cerevisiae* transformant. However, the *Saccharomyces cerevisiae* transformant does not have a sufficient rate of utilizing D-xylose, and in the presence of both D-glucose and D-xylose, glucose repression in D-xylose utilization (in the presence of D-glucose, the rate of D-xylose utilization is extremely slowed) is observed. In other words, an effective D-xylose-utilizing technology has yet to be established. Therefore, improvement regarding these points is desired.

Non Patent Literature 2, also relating to a technology involving *Saccharomyces cerevisiae*, discloses a technology to isolate a variant having an improved rate of uptake and assimilation of D-xylose, the variant obtained by creating a *Saccharomyces cerevisiae* transformant that has a disrupted aldose reductase gene and highly expresses a xylulokinase gene, a ribulose 5-phosphate isomerase gene, a ribulose 5-phosphate epimerase gene, a transketolase gene, and a transaldolase gene from *Saccharomyces cerevisiae*, in addition to a xylose isomerase gene from a fungus, *Piromyces* sp., and then performing anaerobic xylose-limited chemostat and subsequent anaerobic automated sequencing-batch reactor, and a D-xylose-utilizing technology with use of the obtained strain. In this technology, the rate of D-xylose utilization is improved as compared in the technologies of the above Patent Literature 1 and Non Patent Literature 1 but still insufficient. In addition, in the presence of both D-glucose and D-xylose, glucose repression in D-xylose utilization is still observed. Therefore, improvement regarding these points is desired.

Patent Literature 2 discloses a D-xylose-utilizing technology with use of a *Zymomonas mobilis* transformant obtained by transferring four genes, that is, a xylose isomerase gene, a xylulokinase gene, a transketolase gene, and a transaldolase gene from *Escherichia coli* via plasmids into wild-type *Zymomonas mobilis* incapable of utilizing D-xylose and by allowing the genes to be expressed.

Patent Literature 3 discloses a D-xylose-utilizing technology with use of a *Zymomonas mobilis* transformant similarly obtained by integrating four genes, that is, a xylose isomerase gene, a xylulokinase gene, a transketolase gene, and a transaldolase gene from *Escherichia coli* into the chromosome of wild-type *Zymomonas mobilis* and by allowing the genes to be expressed, the four genes in the transformant being stabler. In these known technologies, simultaneous utilization of hexose and pentose is achieved to some extent, but the D-xylose consumption rate (utilization rate) is insufficient as compared to the D-glucose consumption rate (utilization rate), and therefore, further improvement is needed for establishing a practical technology of simultaneous utilization of hexose and pentose.

Although a wild-type strain of *Escherichia coli* is capable of utilizing pentoses including D-xylose, it is known that the above-mentioned glucose repression affects D-xylose utilization in the simultaneous presence of D-glucose and D-xylose. Non Patent Literature 3 and Non Patent Literature 4 report that a microorganism capable of utilizing D-glucose and D-xylose simultaneously can be obtained by disrupting the ptsG (glucose phosphotransferase system (PTS) transport) gene responsible for glucose uptake. However, *Escherichia coli* has a problem of being susceptible to changes in conditions of process operation, resulting in lysis. In addition, the ethanol resistance of *Escherichia coli* is lower than that of *Saccharomyces cerevisia* and *Zymomonas mobilis*. Therefore, ethanol production with use of *Escherichia coli* has a problem of lower final concentration of ethanol (enormous energy is required for concentration and purification of ethanol from fermentation broth).

*Corynebacterium glutamicum* and recombinant strains thereof are useful microorganisms for effective utilization of saccharides because they can produce organic compounds, without proliferation of themselves, in bioconversion from saccharides to organic compounds, such as an organic acid, under reducing conditions (Patent Literature 4). In addition, since no reactor volume for proliferation is needed, it is possible to design a compact reactor. The inventors have already disclosed a technology in which a pyruvate decarboxylase gene and an alcohol dehydrogenase gene derived from *Zymomonas mobilis* are transferred into *Corynebacterium glutamicum* and expressed for highly effective production of ethanol (Non Patent Literature 5).

In a fermentation process in which a microorganism that proliferates in material production, for example, *Saccharomyces cerevisiae*, *Zymomonas mobilis*, or *Escherichia coli*, is used, a major problem is catabolite repression caused by so-called "fermentation inhibitors" (proliferation inhibitors), such as phenols, furans, and organic acids, produced in a pretreatment step necessary for obtaining, as raw materials, saccharides from cellulosic biomass. It has become clear that a technology involving *Corynebacterium glutamicum* has an advantage of being free from catabolite repression caused by so-called "fermentation inhibitors" (proliferation inhibitors) for the reason that the technology enables bioconversion to organic compounds, such as organic acids, without proliferation (Non Patent Literature 6).

However, while having an ability of bioconversion with various advantages, a wild-type strain of *Corynebacterium glutamicum* is originally incapable of utilizing pentoses, such as D-xylose. In this context, the inventors have already disclosed a technology for providing *Corynebacterium glutamicum* with a D-xylose-utilizing ability by transferring a xylose isomerase gene and a xylulokinase gene derived from *Escherichia coli*, and allowing them to be expressed (Non Patent Literature 7).

However, even in the recombinant strain of *Corynebacterium glutamicum* having a D-xylose-utilizing ability, the D-xylose utilization rate is not sufficient as compared with the D-glucose utilization rate. Therefore, further improvement in the D-xylose utilization rate has been required.

Meanwhile, the inventors have proposed a technology of providing *Corynebacterium glutamicum* with an ability of utilizing L-arabinose, a kind of pentoses contained in a cellulosic biomass raw material (Patent Literature 5).

Specifically, in the technology of Patent Literature 5, an arabinose isomerase gene, a ribulokinase gene, and ribulose-5-phosphate-4-epimerase gene derived from *Escherichia coli* are transferred into *Corynebacterium glutamicum* R (FERM P-18976) incapable of utilizing L-arabinose, and allowed to be expressed. Then, into the resultant coryneform bacterium transformant, an L-arabinose transport system proton symporter derived from *Corynebacterium glutamicum* ATCC31831 is transferred. The newly created transformant has a considerably improved L-arabinose utilization rate and, in the presence of both D-glucose and L-arabinose, can perfectly utilize D-glucose and L-arabinose in a simultaneous manner because glucose repression in L-arabinose utilization is completely canceled.

However, as mentioned above, no *corynebacterium* transformant in which glucose repression in D-xylose utilization in the presence of both D-glucose and D-xylose is completely canceled and effective simultaneous parallel utilization of D-glucose and D-xylose is achieved has yet been developed.

CITATION LIST

Patent Literatures

[PTL 1] U.S. Pat. No. 5,789,210
[PTL 2] WO 02/38740
[PTL 3] U.S. Pat. No. 7,354,755
[PTL 4] WO 01/96573 A1
[PTL 5] JP Application No. 2007-222439 (JP 2009-50236 A)

Non Patent Literatures

[NPL 1] Applied and Environmental Microbiology, Vol. 64, 1852-1859 (1998)
[NPL 2] FEMS Yeast Research, Vol. 5, 925-934 (2005)
[NPL 3] Applied Microbiology and Biotechnology, Vol. 56, 120-125 (2001)
[NPL 4] Applied Microbiology and Biotechnology, Vol. 57, 186-191 (2001)
[NPL 5] Journal of Molecular Microbiology and Biotechnology, Vol. 8, 243-254 (2004)
[NPL 6] Applied and Environmental Microbiology, Vol. 73, 2349-2353 (2007)
[NPL 7] Applied and Environmental Microbiology, Vol. 72, 3418-3428 (2006)

SUMMARY OF INVENTION

Technical Problem

An object of the present invention is to provide a recombinant microorganism having an improved D-xylose-utilizing ability, which is necessary for effective utilization of cellulosic biomass, and to provide a method of producing an organic compound with use of the microorganism.

Solution to Problem

The present inventors made extensive examination to achieve the object described above, and found that a transformant created by transferring a specific exogenous gene, that is, an exogenous gene which encodes a protein having a sugar transporter function into a coryneform bacterium, effectively produces an organic compound from D-xylose.

Specifically, the present inventors found a surprising fact that transferring an L-arabinose transport system proton symporter gene derived from *Corynebacterium glutamicum* ATCC31831 into the above-mentioned *Corynebacterium glutamicum* provided with a D-xylose-utilizing ability considerably improves the rate of D-xylose utilization without giving any substrate specificity, and completely cancels glucose repression in D-xylose utilization in the presence of both D-glucose and D-xylose, enabling simultaneous parallel utilization of D-glucose and D-xylose.

As used herein, a coryneform bacterium transformant "is capable of simultaneous parallel utilization of D-xylose and D-glucose (or D-glucose, D-xylose, and L-arabinose)" or "has capability of simultaneous utilization" means that, when the transformant is used to produce an organic compound in a culture medium containing mixed D-xylose and D-glucose (or mixed D-glucose, D-xylose, and L-arabinose) as carbon sources, the transformant is capable of utilizing these carbon sources in parallel and simultaneously at an almost equivalent utilization rate.

The present invention, which has been completed based on the above-mentioned findings, provides the following microorganism and method for producing organic compounds. The recombinant microorganism of the present invention, which has an excellent capability of simultaneous utilization of D-glucose and D-xylose, leads to a technology that provides a process for producing a useful organic compound from a cellulosic biomass raw material, process which is easy to design and operate.

(1) A coryneform bacterium transformant prepared by transferring an exogenous gene which encodes a protein having a sugar transporter function into a coryneform bacterium capable of utilizing D-xylose.
(2) The coryneform bacterium transformant of the above (1), wherein the protein having a sugar transporter function is an L-arabinose transport system proton symporter.
(3) The coryneform bacterium transformant of the above (1) or (2), wherein the exogenous gene which encodes a protein having a sugar transporter function is a DNA comprising the base sequence of SEQ ID NO: 13, or a DNA which hybridizes to a DNA comprising a complementary base sequence of SEQ ID NO: 13 under stringent conditions and which encodes a polypeptide having a sugar transporter function.
(4) The coryneform bacterium transformant of any of the above (1) to (3), wherein the coryneform bacterium capable of utilizing D-xylose is a strain provided with a D-xylose-utilizing ability and selected from the group consisting of *Corynebacterium glutamicum* R (FERM P-18976); FERM P-18979, FERM P-18977, and FERM P-18978, each of which is a recombinant or variant strain capable of utilizing cellobiose; FERM P-19446 and FERM P-19477, each of which is a recombinant strain for succinic acid production; and FERM P-17887, FERM P-17888, FERM P-19361, and FERM P-19362, each of which is a recombinant strain for ethanol production.
(5) The coryneform bacterium transformant of the above (1) or (2), wherein the exogenous gene which encodes a protein having a sugar transporter function is an araE gene derived from a microorganism selected from the group consisting of *Corynebacterium glutamicum* ATCC31831, *Escherichia coli*, *Bacillus subtilis*, *Bacillus licheniformis*, *Bacillus coagulans*, *Lactobacillus sakei*, *Pediococcus pentosaceus*, *Lactobacillus reuteri*, *Oceanobacillus iheyensis*, *Lactococcus lactis*, *Leuconostoc mesenteroides*, *Lactobacillus plantarum*, *Lactobacillus fermentum*, *Lactobacillus brevis*, *Leuconostoc citreum*, *Enterococcus faecium*, *Klebsiella oxytoca*, and *Salmonella typhimurium*.
(6) The coryneform bacterium transformant of any of the above (1) to (5), which is capable of simultaneous parallel utilization of D-glucose and D-xylose.
(7) The coryneform bacterium transformant of the above (6), which is capable of simultaneous parallel utilization of D-glucose, D-xylose, and L-arabinose.
(8) The coryneform bacterium transformant of the above (1), which is *Corynebacterium glutamicum* Ind-araE/pCRA811 (Accession Number: NITE BP-576).
(9) The coryneform bacterium transformant of the above (1), which is *Corynebacterium glutamicum* X5-Ind-araE/Plac-araBAD (Accession Number: NITE BP-577).
(10) The coryneform bacterium transformant of the above (1), which is *Corynebacterium glutamicum* X5-Ind-araE-Δldh/pEthAra (Accession Number: NITE BP-581).
(11) A method for producing an organic compound, which comprises a step of producing an organic compound with use of the coryneform bacterium transformant of any one of the above (1) to (10) in a culture medium containing D-xylose, and a step of collecting the organic compound from the culture medium.
(12) The method of the above (11), wherein the organic compound is at least one kind selected from the group consisting of ethanol, lactic acid, succinic acid, xylitol, acetic acid, and an amino acid.

Advantageous Effects of Invention

The present invention enables effective utilization of D-xylose and simultaneous parallel utilization of D-glucose and D-xylose at an almost equivalent utilization rate. Therefore, effective utilization of a cellulosic biomass resource for producing a useful organic compound can be achieved through an effective reasonable process.

Figure 1:
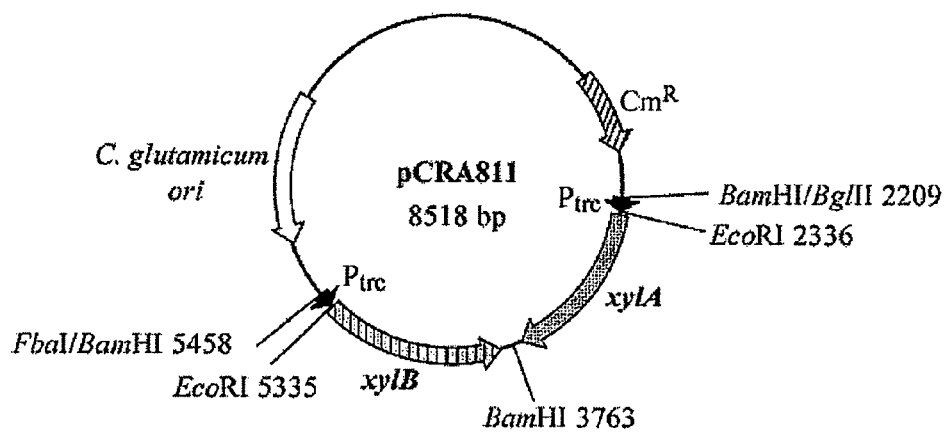
FIG. 1 is a schematic view showing the vector pCRA811 prepared in Example 1 (1).

DESCRIPTION OF EMBODIMENTS (I) Coryneform Bacterium Transformant Having Improved D-Xylose-Utilizing Ability The coryneform bacterium transformant of the present invention is prepared by transferring an exogenous gene which encodes a protein having a sugar transporter function into a coryneform bacterium capable of utilizing D-xylose.

Transferring an exogenous gene which encodes a protein having a sugar transporter function into a coryneform bacterium capable of utilizing D-xylose significantly improves the D-xylose utilizing ability of the coryneform bacterium. As a result, the coryneform bacterium transformant is capable of simultaneous parallel utilization of D-glucose and D-xylose.

In the present invention, the coryneform bacterium capable of utilizing D-xylose, into which an exogenous gene which encodes a protein having a sugar transporter function is transferred later, is not particularly limited as long as the coryneform bacterium is provided with D-xylose utilizing ability. A wild-type strain of a coryneform bacterium is incapable of utilizing pentoses, such as D-xylose. The method of providing a coryneform bacterium with D-xylose utilizing ability is not particularly limited, and examples of such a method include a method in which a D-xylose metabolism-related gene derived from another species is transferred into the coryneform bacterium.

The metabolism from D-xylose to D-xylulose-5-phosphate in procaryotes and some kinds of fungi is, specifically, performed in two steps catalyzed by two enzymes, (a) xylose isomerase that catalyzes a reaction from D-xylose to D-xylulose (hereinafter the enzyme and the gene will be abbreviated to "XylA" and "xylA", respectively) and (b) xylulokinase that catalyzes a reaction from D-xylulose to D-xylulose-5-phosphate (hereinafter the enzyme and the gene will be abbreviated to "XylB" and "xylB", respectively). This metabolic system can be used in the present invention. Transferring the above (a) and (b) genes, which encode these enzymes, into a coryneform bacterium, provides the bacterium with D-xylose utilizing ability. The kind and combination of the original microorganism, the order of transfer, etc. of the above (a) and (b) genes are not particularly limited as long as the polypeptides encoded by the genes have D-xylose metabolizing ability.

For example, the inventors have already disclosed a technology for providing a coryneform bacterium with a D-xylose-utilizing ability by transferring a xylose isomerase gene (xylA) and a xylulokinase gene (xylB) derived from *Escherichia coli* as D-xylose metabolism-related genes, and allowing them to be expressed (Non Patent Literature 7). In the present invention, a coryneform bacterium which is prepared by such a technology and thereby provided with D-xylose utilizing ability can be used. In order to prepare a transformant provided with D-xylose utilizing ability, the transferred gene may be derived from a species other than the above-mentioned *Escherichia coli*.

The above two genes (a) and (b), which encode the D-xylose metabolism-related enzymes, may exist on the same locus or on different loci. Examples of the case where the two genes exist on the same locus include an operon formed of the above genes (a) and (b) linked to each other.

Microorganisms capable of utilizing D-xylose usually carry the above genes (a) and (b). In the present invention, it is preferred to use, as the above genes (a) and (b), a xylA gene and a xylB gene derived from a same or different microorganism selected from the group consisting of *Escherichia coli*, *Corynebacterium glutamicum* (having a xylB gene only), *Bacillus subtilis*, *Salmonella typhimurium*, *Bacillus halodurans*, *Sinorhizobium meliloti*, and *Agrobacterium tumefaciens*.

Use of a xylA gene and a xylB gene derived from, inter alia, *Escherichia coli* is most preferred.

As the genes that encode the D-xylose metabolism-related enzymes, when the base sequences of DNA fragments comprising the above genes (a) and (b) are known, DNA fragments synthesized based on the sequences may be used. Even when the DNA sequences are unknown, necessary fragments can be obtained by a hybridization method and the PCR method based on amino acid sequences conserved among D-xylose metabolism-related enzyme proteins. Further, DNA fragments can be obtained by degenerate PCR with use of mixed primers designed based on known sequences of other D-xylose metabolism-related genes.

In the genes that encode the D-xylose metabolism-related enzymes, as long as the D-xylose metabolism-related activity of the polypeptides encoded by the genes is maintained, a part of the base sequence may be substituted or deleted. Also, a base may be newly inserted, and a part of the base sequence may be transposed. Any of these derivatives of the genes that encode the D-xylose metabolism-related enzymes may be used in the present invention. The above-mentioned "a part of the base sequence" may be, for example, one to several (usually 1 to 5, preferably 1 to 3, and more preferably 1 to 2) in terms of amino-acid residues.

The base sequence of the gene which encodes a D-xylose metabolism-related enzyme preferably encodes a D-xylose metabolism-related enzyme derived from procaryote, that is, a D-xylose metabolism-related enzyme having the same amino acid sequence as that of D-xylose metabolism-related enzyme found in procaryote in nature. As compared with a D-xylose metabolism-related enzyme derived from eukaryote, a D-xylose metabolism-related enzyme of procaryote, when expressed, enhances the possibility that the D-xylose metabolism-related enzyme is expressed in an activated form in bacteria.

The coryneform bacterium as a host is not particularly limited as long as it has a function of metabolic conversion of saccharides. Depending on the kind of saccharides or the kind of objective organic compounds, additional functions that are not natural functions of a coryneform bacterium, such as a pathway of saccharide uptake and metabolism, or a pathway of conversion to the objective organic compound may be needed. In such cases, such functions may be provided by genetic recombination, mutagenesis, or the like.

The coryneform bacterium used in the present invention belongs to a group of microorganisms defined in Bargeys Manual of Determinative Bacteriology, Vol. 8, 599 (1974), and is not particularly limited as long as it proliferates under normal aerobic conditions. The specific examples include *Corynebacterium*, *Brevibacterium*, *Arthrobacter*, *Mycobacterium* and *Micrococcus*.

Further specifically, examples of the *Corynebacterium* include *Corynebacterium glutamicum* R (FERM P-18976), ATCC13032, ATCC13058, ATCC13059, ATCC13060, ATCC13232, ATCC13286, ATCC13287, ATCC13655, ATCC13745, ATCC13746, ATCC13761, ATCC14020 and ATCC31831.

Examples of the *Brevibacterium* include *Brevibacterium lactofermentum* ATCC13869; *Brevibacterium flavum* MJ-233 (FERM BP-1497) and MJ-233AB-41 (FERM BP-1498); and *Brevibacterium* ammonia genes ATCC6872.

Examples of the *Arthrobacter* include *Arthrobacter globiformis* ATCC8010, ATCC4336, ATCC21056, ATCC31250, ATCC31738 and ATCC35698.

Examples of the *Mycobacterium* include *Mycobacterium bovis* ATCC19210 and ATCC27289.

Examples of the *Micrococcus* include *Micrococcus freudenreichii* NO. 239 (FERM P-13221), *Micrococcus leuteus* NO. 240 (FERM P-13222), *Micrococcus ureae* IAM1010, and *Micrococcus roseus* IF03764.

The coryneform bacterium is preferably capable of actively or passively transporting D-xylose into cells. In addition, the coryneform bacterium to be transformed preferably has a glycolytic pathway and a pentose phosphate pathway that function in a normal manner. Further, the coryneform bacterium to be transformed preferably contains an enzyme for converting pyruvic acid into the objective fermentation product, for example, succinic acid, acetic acid, or lactic acid.

Further, the coryneform bacterium to be used is preferably highly resistant to ethanol; organic acids, such as lactic acid, acetic acid, and formic acid; and sugar-degraded products, such as furfural and hydroxymethylfurfural. In this context, the coryneform bacterium to be used in the present invention is preferably *Corynebacterium glutamicum* R (FERM P-18976, JP Application No. 2002-252190 (JP 2004-089029 A)), *Corynebacterium glutamicum* ATCC31831, or the like.

The coryneform bacterium may be a natural variant strain of a wild-type strain (for example, a variant strain capable of utilizing cellobiose: FERM P-18977, FERM P-18978) (JP Application No. 2002-252190 (JP 2004-089029 A)), or an artificial recombinant strain, etc. Example of the artificial recombinant strains include, for example, recombinant strains for ethanol production (FERM P-17887 (FERM BP-7621), FERM P-17888 (FERM BP-7622) (PCT/JP01/04935 (WO 01/096573)), and strains described in J. Mol. Microbiol. Biotechnol., Vol. 8, 243-254 (2004) (FERM P-19361 and FERM P-19362 described in Japanese Patent No. 42943735)); recombinant strains utilizing cellobiose (FERM P-18979 (JP Application No. 2002-252190 (JP 2004-089029 A)) etc.); recombinant strains for succinic acid production (FERM P-19446 (FERM BP-10060) and FERM P-19477 (FERM BP-10061)) (FERM P-19446 and FERM P-19477 are the same strains as FERM BP-10060 and FERM BP-10061 described in WO 2005/010182 A1, respectively); etc. The strains described in "J. Mol. Microbiol. Biotechnol., Vol. 8, 243-254 (2004)" (FERM P-19361 and FERM P-19362 described in Japanese Patent No. 42943735) are coryneform bacterium transformants prepared by transferring a pyruvate decarboxylase gene and an alcohol dehydrogenase gene derived from *Zymomonas mobilis* into *Corynebacterium glutamicum*.

In the present invention, the coryneform bacterium capable of utilizing D-xylose is preferably a strain provided with a D-xylose-utilizing ability and selected from the group consisting of *Corynebacterium glutamicum* R (FERM P-18976); recombinant or variant strains capable of utilizing cellobiose (FERM P-18979, FERM P-18977, and FERM P-18978); recombinant strains for succinic acid production (FERM P-19446 and FERM P-19477); and recombinant strains for ethanol production (FERM P-17887 (FERM BP-7621), FERM P-17888 (FERM BP-7622), and strains described in J. Mol. Microbiol. Biotechnol., Vol. 8, 243-254 (2004) (FERM P-19361 and FERM P-19362)).

In the present invention, a particularly preferred coryneform bacterium is *Corynebacterium glutamicum* R (FERM P-18976) to which D-xylose utilizing ability is provided.

Exogenous Gene which Encodes Protein Having Sugar Transporter Function

In the present invention, into a coryneform bacterium capable of utilizing D-xylose, an exogenous gene which encodes a protein having a sugar transporter function (also referred to as a sugar transporter gene) is transferred. Thereby, the D-xylose utilizing ability of the coryneform bacterium transformant can be further improved. The protein having a sugar transporter function may be any protein that is capable of transporting hexose and pentose, and inter alia, an L-arabinose transport system proton symporter is preferred.

In the present invention, as the exogenous gene which encodes a protein having a sugar transporter function, a gene which encodes a protein having an L-arabinose transport system proton symporter function (also referred to as an L-arabinose transport system proton symporter gene) is preferably used. The L-arabinose transport system proton symporter gene is already known, and is called araE. The araE gene sequence and enzymatic characteristics in the following bacterial strains etc. are reported: *Bacillus subtilis* (J. Bacteriol. Vol. 179, 7705-7711 (1997)), *Klebsiella oxytoca* 8017 (J. Bacteriol., Vol. 177, 5379-5380 (1995)), and *Escherichia coli* (J. Biol. Chem., Vol. 263, 8003-8010 (1988)).

In the present invention, as the exogenous gene which encodes a protein having a sugar transporter function, an araE gene derived from a microorganism selected from the group consisting of *Corynebacterium glutamicum* ATCC31831, *Escherichia coli*, *Bacillus subtilis*, *Bacillus licheniformis*, *Bacillus coagulans*, *Lactobacillus sakei*, *Pediococcus pentosaceus*, *Lactobacillus reuteri*, *Oceanobacillus iheyensis*, *Lactococcus lactis*, *Leuconostoc mesenteroides*, *Lactobacillus plantarum*, *Lactobacillus fermentum*, *Lactobacillus brevis*, *Leuconostoc citreum*, *Enterococcus faecium*, *Klebsiella oxytoca*, and *Salmonella typhimurium* may be used.

As an exogenous gene which encodes the protein which has L-arabinose transport system proton symporter activity suitable for the present invention, an araE gene derived from a microorganism selected from the group consisting of *Corynebacterium glutamicum* ATCC31831, *Escherichia coli*, *Bacillus subtilis*, *Klebsiella oxytoca*, and *Salmonella typhimurium* is preferably used. Also, as the L-arabinose transport system proton symporter gene, the DNA sequence represented by SEQ ID NO: 13, or a DNA which hybridizes to a DNA sequence comprising a complementary base sequence of the DNA represented by SEQ ID NO: 13 under stringent conditions and which encodes a polypeptide having a sugar transporter function (for example, L-arabinose transport system proton symporter function) is preferably used. That is, in the present invention, as the exogenous gene which encodes a protein having a sugar transporter function, a DNA comprising the base sequence represented by SEQ ID NO: 13, or a DNA which hybridizes to a DNA comprising a complementary base sequence of SEQ ID NO: 13 under stringent conditions and which encodes a polypeptide having a sugar transporter function is preferably used. The DNA having the base sequence of SEQ ID NO: 13 is the araE gene derived from *Corynebacterium glutamicum* ATCC31831. A suitable method for regulating the expression level of the araE gene in a D-xylose utilizing strain is well known in the art. In the present invention, the kind and combination of the original microorganism, the order of transfer, etc. of the above D-xylose metabolism-related enzyme gene and the sugar transporter gene are not particularly limited.

Here, "stringent conditions" means conditions where hybridization occurs with 90% or more, preferably 95% or more, more preferably 97% or more, and further more preferably 98% or more sequence homology. Usually, it means conditions where hybridization occurs at a temperature about 5 to 30° C., preferably about 10 to 25° C., and more preferably about 15 to 20° C. below the melting temperature (Tm) of a perfect hybrid. Such "stringent conditions" are described in J. Sambrook et al., Molecular Cloning, A Laboratory Manual, Second edition, Cold Spring Harbor Laboratory Press (1989), particularly in Section 11.45 "Conditions for Hybridization of Oligonucleotide Probes", and the conditions may be used here.

In the present invention, homology values between base sequences were calculated using calculation software GENETYX (registered trademark) Ver. 8 (made by Genetics).

Also, in the present invention, a DNA which hybridizes to a certain DNA under stringent conditions, for example, a DNA which hybridizes to a DNA comprising a complementary base sequence of SEQ ID NO: 13 under stringent conditions has preferably about 90% or more, more preferably about 95% or more, and particularly preferably about 98% or more sequence homology with the base sequence of SEQ ID NO: 13.

The coryneform bacterium transformant of the present invention is preferably capable of simultaneous parallel utilization of D-glucose and D-xylose, and more preferably capable of simultaneous parallel utilization of D-glucose, D-xylose, and L-arabinose.

The coryneform bacterium transformant of the present invention can be prepared by transferring, for example, the above-mentioned sugar transporter gene into a coryneform bacterium capable of utilizing D-xylose. Also, the coryneform bacterium transformant capable of simultaneous parallel utilization of D-glucose, D-xylose, and L-arabinose can be prepared by transferring, for example, the above-mentioned D-xylose metabolism-related enzyme gene and sugar transporter gene, and L-arabinose metabolism-related enzyme gene into a coryneform bacterium. As the L-arabinose metabolism-related enzyme gene, for example, a gene which encodes L-arabinose isomerase, a gene which encodes L-ribulokinase, and a gene which encodes L-ribulose-5-phosphate-4-epimerase of *Escherichia coli* are preferred. The kind and combination of the original microorganism, the order of transfer, etc. of the above D-xylose metabolism-related enzyme gene, the sugar transporter gene, and L-arabinose metabolism-related enzyme gene are not particularly limited.

Construction of Vector

First, an oligonucleotide primer set for amplifying the sequence of the above-mentioned sugar transporter gene, for example, a DNA which encodes an L-arabinose transport system proton symporter (araE, the protein may be called AraE) by PCR (polymerase chain reaction) is prepared. Examples of such a primer set include, for example, a primer set consisting of the base sequences of SEQ ID NOs: 14 and 15. In the PCR method, a known PCR device, for example a thermal cycler, may be used. The PCR cycle may be performed according to known techniques. For example, a cycle of denaturation, annealing and extension is repeated usually 10 to 100 times, preferably about 20 to 50 times. Templates used in the PCR to synthesize cDNA of an AraE-encoding DNA may be DNA isolated from a microorganism having a sugar transporter gene. A gene obtained by the PCR method may be transferred into a suitable cloning vector. In a cloning process, a commercially available PCR cloning system etc. [pGEM-T easy vector system (made by Promega), TOPO TA-cloning system (made by Invitrogen), Mighty Cloning Kit (made by Takara), etc.] can also be used. Alternatively, by a hybridization method using, as a template, synthetic primers suitably designed based on a known base sequence of AraE-encoding DNA, a DNA fragment comprising the corresponding region may be obtained. An example of such a method will be described in detail in Examples.

Subsequently, a cloning vector comprising a gene obtained by the PCR method is transferred into a microorganism, for example, *Escherichia coli* JM109 strain for transformation. The transformed strain is cultured in a culture medium containing suitable antibiotics (for example, ampicillin, chloramphenicol, etc.), and cells are collected from the culture. From the collected cells, plasmid DNA is extracted. The extraction of the plasmid DNA can be performed using a known technique. A commercial plasmid extraction kit may also be used for easy extraction. Examples of the commercial plasmid extraction kit include Qiaquick plasmid extraction kit (trade name) made by QIAGEN. By determining the base sequence of this extracted plasmid DNA, the existence of the sequences of an AraE-encoding gene can be confirmed. The base sequence of the DNA can be determined by a known method, for example, the dideoxy chain termination method etc. Alternatively, the base sequence can also be determined using a capillary electrophoretic system which utilizes multi-fluorescence technique for detection. Alternatively, the base sequence can also be determined using a DNA sequencer, for example, ABI PRISM 3730×1 DNA Analyzer (made by Applied Biosystem) etc.

The above-mentioned methods can be performed in the usual manner of genetic engineering experiments. Vectors of various kinds of microorganisms, and methods for transfer and expression of exogenous genes are described in many experimental books (for example, Molecular Cloning: A Laboratory Manual (3rd Edition) CSHL Press (2001), or Current protocols in molecular biology. Green Publishing and Wiley InterScience, New York (1987), etc.). Therefore, selection of vectors, and transfer and expression of genes can be performed according to these books.

Next, an araE gene is expressed on a plasmid or a chromosome in the above-mentioned coryneform bacterium capable of utilizing D-xylose. For example, using a plasmid, these genes are transferred under a regulatory sequence so as to be expressible. Herein, "under a regulatory sequence" means that cooperative work of these genes with, for example, a promoter, an inducer, an operator, a ribosome binding site and a transcription terminator can achieve transcription and translation. A plasmid vector used for such a purpose may be any plasmid vector as long as it comprises a gene responsible for autonomously replicating function in a coryneform bacterium. Specific examples of the plasmid vector include pAM330 derived from *Brevibacterium lactofermentum* 2256 (JP 58-67699 A; Agric. Biol. Chem. Vol. 48, 2901-2903 (1984); and Nucleic Acids Symp. Ser. Vol. 16, 265-267 (1985)); pHM1519 derived from *Corynebacterium glutamicum* ATCC13058 (Agric., Biol., Chem. Vol. 48, 2901-2903 (1984)) and pCRY30 derived from the same (Appl. Environ. Microbiol. Vol. 57, 759-764 (1991)); pCG4 derived from *Corynebacterium glutamicum* T250 (JP 57-183799 A; and J. Bacteriol., Vol. 159, 306-311 (1984)), pAG1, pAG3, pAG14 and pAG50 derived from the same (JP 62-166890 A), and pEKO, pEC5 and pEKExl derived from the same (Gene, Vol. 102, 93-98 (1991)); plasmids derived therefrom; etc. The vector preferably comprises a multicloning site which comprises various kinds of restriction enzyme sites inside, or a single restriction enzyme site.

A wide variety of promoters can suitably be used in the present invention. Such a promoter may be obtained from many known supply sources including yeast, bacteria, and other cell supply sources and may have any base sequence as long as it has a function to start transcription of a target gene in a coryneform bacterium. The promoter used in the present invention is preferably an effective non-glucose-repression promoter. Preferred examples of such a promoter include the lac promoter, the trc promoter, the tac promoter, etc., which are known as strong constitutive promoters in coryneform bacteria. The promoter used in the present invention may be modified for change in its regulatory mechanism. The terminator placed downstream of a target gene under a regulatory sequence may also have any base sequence as long as it has a function to terminate transcription of the gene in a coryneform bacterium.

The plasmid vector used for creating a coryneform bacterium transformant of the present invention, for example in the case where the araE gene derived from *Corynebacterium glutamicum* ATCC31831 is used, can be constructed by ligating each of the genes whose base sequences have already been confirmed to a suitable regulatory sequence such as promoters and terminators, and subsequently inserting the ligated genes in a suitable restriction enzyme site of one of the above-mentioned plasmid vectors. Details are described in Examples.

Transformation

The method for transferring a plasmid vector comprising an objective gene into a coryneform bacterium is not particularly limited as long as the transfer of the objective gene into the coryneform bacterium can be achieved, and examples of such a method include an electric pulse method (electroporation) and a $CaCl_2$ method. Specific examples that can be used include a known electric pulse method (Agric. Biol. Chem., Vol. 54, 443-447 (1990) or Res. Microbiol., Vol. 144, 181-185 (1993)).

To collect the coryneform bacterium transformant of the present invention, according to the conventional method, a drug-resistant gene etc. is transferred into a plasmid comprising the objective gene, the coryneform bacterium treated for transfer of the objective gene is applied onto a plate culture medium containing the drug in an appropriate concentration, and then the coryneform bacterium transformant can be selected. Specific examples of the method include the method described in Agric. Biol. Chem., Vol. 54, 443-447 (1990) or Res. Microbiol., Vol. 144, 181-185 (1993).

Specific examples of the coryneform bacterium transformant created by the above-mentioned method include *Corynebacterium glutamicum* Ind-araE/pCRA811 (Accession Number NITE BP-576) and *Corynebacterium glutamicum* X5-Ind-araE/Plac-araBAD (Accession Number NITE BP-577), both of which were deposited in Incorporated Administrative Agency National Institute of Technology and Evaluation, NITE Patent Microorganisms Depositary (2-5-8 Kazusakamatari, Kisarazu-shi, Chiba 292-0818 Japan) on May 28, 2008; and *Corynebacterium glutamicum* X5-Ind-araE-Δldh/pEthAra (Accession Number NITE BP-581), which was deposited in Incorporated Administrative Agency National Institute of Technology and Evaluation, NITE Patent Microorganisms Depositary (2-5-8 Kazusakamatari, Kisarazu-shi, Chiba 292-0818 Japan) on Jun. 4, 2008. These coryneform bacterium transformants are capable of simultaneous parallel utilization of D-glucose and D-xylose, and therefore, can be suitably utilized in a culture medium containing D-xylose and D-glucose resources as described below.

For improving production of an organic compound, the transformant created in the present invention may further comprise genetic modification which leads to one or more characteristics selected from the group consisting of increased flow in pentose phosphate pathway, increased resistance to ethanol, osmotic pressure or organic acids, and reduced production of by-products (carbon-containing molecules other than the target product). Such genetic modification can be introduced, in particular, for example, by overexpression of an exogenous gene and/or inactivation of an endogenous gene, classic mutagenesis, screening and/or target variant selection.

The thus created coryneform bacterium transformant of the present invention can produce, in the reaction mixture, various organic compounds, such as monocarboxylic acids, dicarboxylic acids, ketocarboxylic acids, hydroxycarboxylic acids, amino acids, monoalcohols, polyols and vitamins from D-xylose (when a polycarboxylic acid which exists in the TCA pathway is produced, a carbonate ion, etc. is further used as a raw material) at a high rate of production and at a high concentration of accumulated product while improving the metabolic rate of saccharides or inhibiting time-dependent decline in the metabolic rate of saccharides.

(II) Method for Producing Organic Compound

Proliferation Culture Step

To produce an organic compound with use of the coryneform bacterium transformant of the present invention, it is preferred to carry out proliferation culture of the coryneform bacterium transformant under aerobic conditions first.

The coryneform bacterium transformant can be cultured in an ordinary nutritive medium containing a carbon source, a nitrogen source, inorganic salts, etc. In the culture, carbon sources, such as glucose and blackstrap; and nitrogen sources, such as ammonia, ammonium sulfate, ammonium chloride, ammonium nitrate, and urea; each can be used alone or in combination of two or more kinds thereof. Examples of the inorganic salts that can be used include potassium hydrogen phosphate, potassium dihydrogen phosphate, magnesium sulfate, and the like. In addition, nutrients including peptone, meat extract, yeast extract, corn steep liquor, casamino acids, and various vitamins, such as biotin and thiamine, may be added to the culture medium if needed.

The culture can be performed under aerobic conditions, such as stirring with aeration or shaking, at about 14 to 45° C., preferably at about 25 to 37° C. The pH of the culture medium during the culture is preferably about 5 to 10, more preferably about 6.5 to 8.5. The pH can be adjusted by adding an acid or an alkali. The carbon source concentration in the culture medium at the start of culture is preferably about 1 to 20% (w/v), more preferably about 2 to 5% (w/v). The culture period is usually about 1 to 7 days.

Subsequently, cultured bacterial cells of the coryneform bacterium transformant are collected. The method for collecting and isolating cultured bacterial cells from the culture obtained as described above is not particularly limited, and any known method, such as centrifugal separation and membrane separation, may be used.

The collected bacterial cells may be subjected to some treatment and then the resulting treated bacterial cells may be used in the next step. As long as the cultured bacterial cells have undergone some treatment, they can be used as the treated bacterial cells. Examples of the treated bacterial cells include immobilized bacterial cells obtained by treatment with, for example, acrylamide, carrageenan, or the like.

The cultured bacterial cells of the coryneform bacterium transformant collected and isolated from the culture or treated bacterial cells thereof obtained as described above are subjected to a step of producing an organic compound (also referred to as an organic compound producing step).

Organic Compound Producing Step

In the organic compound producing step, an organic compound is produced in a culture medium containing D-xylose (reaction medium) with use of the above coryneform bacterium transformant. The method for producing an organic compound including such a step is also included in the present invention.

The reaction medium contains D-xylose as a carbon source, and may further contain D-glucose. The D-xylose or D-glucose may be D-xylose or D-glucose itself, or an oligomeric or polymeric carbohydrate which comprises D-xylose units or D-glucose units, such as lignocellulose, arabinan, cellulose, and starch. To release the D-xylose units or the D-glucose units from the carbohydrate, a suitable carbohydrase (xylanase, glucanase, amylase, etc.) may be added to the reaction medium. Alternatively, a coryneform bacterium transformant may be made to produce the enzyme.

The reaction medium may contain organic carbon sources other than D-xylose and D-glucose. Such organic carbon sources include saccharides that the coryneform bacterium transformant of the present invention can utilize for a biochemical reaction.

Specific examples of the saccharides include monosaccharides such as (D- or L-) arabinose, galactose, fructose and mannose; disaccharides such as cellobiose, sucrose, lactose and maltose; polysaccharides such as dextrin and soluble starch; etc. In particular, monosaccharides such as C6 sugars and C5 sugars are preferred, and inter alia, L-arabinose is preferred.

More preferably, the reaction medium used for a reaction for producing an organic compound contains ingredients necessary for the coryneform bacterium transformant or treated transformant to maintain its metabolic functions, that is, carbon sources such as various saccharides; nitrogen sources necessary for protein synthesis; and others including salts of phosphorus, potassium, sodium, etc. and salts of trace metals such as iron, manganese and calcium. The amounts of such ingredients may be suitably determined depending on the necessary reaction time, the target organic compound, or the coryneform bacterium transformant to be used. Depending on the coryneform bacterium transformant to be used, addition of certain vitamins may be preferred. The carbon source, the nitrogen source, the inorganic salt, the vitamin, and the trace metal salt to be used may be known ingredients, for example, those illustrated in the proliferation culture step.

The pH of the reaction medium is preferably about 6 to 8.

The reaction of the coryneform bacterium transformant or treated bacterial cells thereof with the carbon source containing D-xylose is preferably performed under temperature conditions in which the coryneform bacterium transformant of the present invention or treated bacterial cells thereof can work. The temperature may be suitably determined depending on the coryneform bacterium transformant or treated bacterial cells thereof, etc. The temperature is usually about 25 to 35° C. Relating also to the method of carbon dioxide encapsulation of the reaction system, depending on the objective organic compound, it may be effective to inject carbon dioxide or various kinds of inorganic carbonates, such as carbonates or hydrogencarbonates, in addition to organic carbon sources, such as saccharides, to the reaction medium. The concentration of the carbon source in the culture medium is not particularly limited and usually about 0.1 to 30% by mass, preferably about 0.5 to 20% by mass. The mixing ratio (mass ratio) of sugars (D-xylose/D-glucose) in the carbon source depends on the kind of biomass raw material, and is usually about ⅓ to ⅔. For example, in cases where the carbon source in the reaction medium comprises various kinds of C6 sugars and C5 sugars, the mixing ratio of C5 sugars to C6 sugars (mass ratio of C5 sugars to C6 sugars) is usually about ¼ to ¾.

In the organic compound producing step, the reaction medium is preferably under reducing conditions. That is, the coryneform bacterium transformant or treated bacterial cells thereof are subjected to the reaction for producing an objective organic compound preferably under reducing conditions. The method for producing an organic compound may be any of a batch method, a fed-batch method, and a continuous method.

In the present invention, producing an organic compound in a reaction medium under reducing conditions with use of a coryneform bacterium transformant, that is, producing an organic compound by a biochemical reaction under reducing conditions, enables complete inhibition of the proliferation through division of the coryneform bacterium transformant of the present invention, and thereby enables substantially complete inhibition of secreted by-products accompanying the proliferation. From this point of view, when a coryneform bacterium transformant or treated cells thereof collected from the culture proliferation step are used in a reaction medium, it is preferred to adopt methods and conditions that can prevent the environmental conditions in and out of the coryneform bacterium at the time of aerobic proliferation from being brought into the reaction medium. That is, it is preferred that the reaction medium does not substantially contain any products produced during the culture proliferation step and existing in and out of the bacterial cells. More specifically, it is preferred that the reaction medium substantially contains neither the by-products produced and secreted outside the bacterial cells in the culture proliferation step nor substances produced through aerobic metabolism functions in the cultured bacterial cells and remaining inside the cells. Such conditions can be achieved by centrifugal separation, membrane separation, or other treatment of the culture medium after proliferating culture, and/or by leaving the bacterial cells after culture under reducing conditions for about 2 to 10 hours.

In this step, the reaction medium is preferably under reducing conditions, and the reaction medium may be in any state of solid, semi-solid, liquid, and the like.

In the present invention, "a reducing condition" is defined based on the redox potential of the reaction system (reaction medium), and means that the redox potential of the reaction medium is negative (−). The redox potential of the reaction medium under reducing conditions is preferably about −200 mV to −500 mV, more preferably about −250 mV to −500 mV.

The reducing condition of the reaction medium can be simply estimated to some extent with use of resazurin indicator (in reducing conditions, decolorization from blue to colorless is observed). However, for precise measurement, a redox-potential meter (for example, ORP Electrodes made by BROADLEY JAMES) is used. In the present invention, it is preferred that reducing conditions are maintained from immediately after addition of cells or treated cells to the reaction medium until collection of an organic compound, and it is necessary that the reaction medium is under reducing conditions at least at the time of organic compound collection. The reaction medium is maintained in reducing conditions preferably for about 50% or more, more preferably for about 70% or more, further more preferably for about 90% or more of the reaction time. It is particularly preferred that the redox-potential of the reaction medium is maintained from about −200 mV to −500 mV preferably for about 50% or more, more preferably for about 70% or more, further more preferably for about 90% or more of the reaction time.

Such reducing conditions can be achieved, in particular, through a method for preparing cultured bacterial cells after the above-described culture, a method for preparing a reaction medium, or a method for maintaining reducing conditions during the reaction. As the method for preparing a reaction culture medium under reducing conditions, a publicly known method may be used. As the method for preparing an aqueous solution for the reaction medium, for example, the method for preparing a culture medium for strictly anaerobic microorganisms, such as sulfate-reducing microorganisms [The dissimilatory sulfate-reducing bacteria, In The Prokaryotes, A Handbook on Habitats, Isolation and Identification of Bacteria, Ed. by Starr, M. P. et. al. Berlin, Springer Verlag, 926-940 (1981), or Kyoto Daigaku Nogakubu Nogeikagaku Kyoshitu, Nogeikagaku Jikkensho, Vol. 3, Sangyo Tosho (1990), Issue 26] may be used to obtain an aqueous solution under desired reducing condition.

More specific examples of the method for preparing a reaction medium include a method in which dissolved gases are removed by heat-treatment or decompression treatment of the reaction medium. More specifically, a reaction medium under reducing conditions can be prepared by removing dissolved gases, especially dissolved oxygen, by treating the reaction medium under reduced pressure of about 10 mmHg or less, preferably about 5 mmHg or less, more preferably about 3 mmHg or less, for about 1 to 60 minutes, preferably for about 5 to 40 minutes. Alternatively, by adding a suitable reducing agent (for example, thioglycolic acid, ascorbic acid, cysteine hydrochloride, mercaptoacetic acid, thiol acetic acid, glutathione, sodium sulfide, etc.), a reaction medium under reducing conditions can be prepared. These methods may be suitably combined to prepare an effective reaction medium under reducing conditions in some cases.

As the method for maintaining reducing conditions during the reaction, it is preferred that oxygen from the outside of the reaction system is prevented to the utmost extent from entering the system. For this purpose, a method of encapsulating the reaction system with inert gas, such as nitrogen gas, carbon dioxide gas, etc. is usually used. In some cases, for allowing the metabolic functions in the cells of a coryneform bacterium transformant to work effectively, addition of a solution of various nutrients or a reagent solution for adjusting and maintaining the pH of the reaction system may be needed. In such a case, for more effective prevention of oxygen incorporation, it is effective to remove the oxygen in the solutions to be added, in advance.

Finally, the organic compound produced in the reaction medium as described is collected. The method may be a publicly known method used in the bioprocess. Such publicly known methods include salting-out, recrystallization, extraction with organic solvent, esterification distillation, chromatography, and electrodialysis, and the method for separation, purification, or collection may be appropriately selected according to the characteristics of the organic compound product.

Examples of the organic compound which can be produced by the method of the present invention include organic acids, alcohols, amino acids, and vitamins. Examples of the organic acid include acetic acid, lactic acid, 3-hydroxypropionic acid, acrylic acid, succinic acid, fumaric acid, malic acid, oxalacetic acid, citric acid, cis-aconitic acid, isocitric acid, itaconic acid, 2-oxoglutaric acid, and shikimic acid. Examples of the alcohol include ethanol, butanol, 1,3-propanediol, glycerol, xylitol, sorbitol, and 1,4-butanediol. Examples of the amino acid include valine, leucine, alanine, aspartic acid, lysine, isoleucine, and threonine. The method of the present invention is suitable for production of one or more kinds of organic compounds selected from the group consisting of ethanol, lactic acid, succinic acid, xylitol, acetic acid, and an amino acid.

The present invention further provides a D-xylose utilizing coryneform bacterium transformant with remarkably improved capability to produce an organic compound from D-xylose, or a mixture of D-glucose and D-xylose, by a reaction under the conditions described above.

EXAMPLES

Hereinafter, the present invention will be illustrated in more detail by Examples, but is not limited thereto.

Example 1

Creation of *Corynebacterium glutamicum* R/pCRA811 and *Corynebacterium glutamicum* Ind-araE/pCRA811

(1) Method for Construction of Plasmid pCRA811
a) Extraction of Chromosomal DNA from *Escherichia coli* JM109

*Escherichia coli* JM109 was inoculated in L medium (10 g of trypton, 5 g of yeast extract, and 5 g of NaCl were dissolved in 1 L of distilled water) with use of a platinum loop, and cultured with shaking at 37° C. until logarithmic growth phase, and then cells were collected. According to the instruction manual, chromosomal DNA was recovered from the collected cells with use of a DNA extraction kit (trade name: GenomicPrep Cells and Tissue DNA Isolation Kit, made by Amersham).

b) Cloning of D-Xylose Isomerase Gene (xylA) and D-Xylulokinase Gene (xylB) from *Escherichia coli*

A DNA fragment comprising a xylose isomerase gene (hereinafter abbreviated as xylA) (SEQ ID NO: 1) and a D-xylulokinase gene (hereinafter abbreviated as xylB) (SEQ ID NO: 2) from *Escherichia coli* was amplified by the PCR method as described below.

In the PCR, the following set of primers was synthesized based on the sequence of *Escherichia coli* with use of "394 DNA/RNA Synthesizer" made by Applied Biosystems for cloning of the xylA gene and the xylB gene, and was used.

Primer Set for xylA Gene Amplification

```
                                           (SEQ ID NO: 3)
Primer 1:   5'-CTCTGAATTCACCTGATTATGGAGTTCAAT-3'

(SEQ ID NO: 4)
Primer 2:   5'-CTCTCCCGGGCATATCGATCGTTCCTTAAA-3'
```

Primer Set for xylB Gene Amplification

```
                                           (SEQ ID NO: 5)
Primer 3:   5'-CTCTGAATTCTTTAAGGAACGATCGATATG-3'

(SEQ ID NO: 6)
Primer 4:   5'-CTCTCCCGGGTTCAGAATAAATTCATACTA-3'
```

The forward primers and the reverse primers have an EcoRI site and a SmaI site added to the end thereof, respectively. The chromosomal DNA of the *Escherichia coli* JM109 extracted in the above Example 1 (1) a) was used as template DNA.

PCR was performed with use of "DNA thermal cycler" made by PerkinElmer Cetus and DNA polymerase (trade name: Takara LA Taq HS DNA polymerase, made by Takara Shuzo) as a reaction reagent under the conditions described below.

Reaction Mixture:
(10×) PCR buffer soln.: 10 μL
2.5 mM dNTP Mix: 16 μL
Template DNA: 5 μL (DNA content: 1 μg or less)
The above 2 primers: 1 μL each (final conc.: 0.25 μM)
Takara LA Taq HS DNA polymerase: 1 μL
DMSO: 10 μL (final conc.: 2%)
Sterile distilled water: 57 μL The above ingredients were mixed, and 100 μL of the reaction mixture was subjected to PCR.

PCR cycle:
Denaturation step: 94° C., 1 minute
Annealing step: 55° C., 1 minute
Extension step: 72° C., 2 minutes A cycle consisting of the above 3 steps was repeated 30 times.

With use of part of the thus obtained reaction mixture, 1% (w/v) agarose gel electrophoresis was performed, and an about 1.4-kb DNA fragment comprising the xylA gene and an about 1.6-kb DNA fragment comprising the xylB gene were detected.

The about 1.4-kb amplification product treated with the above-mentioned restriction enzymes EcoRI and SmaI, and the vector pTrc99A (made by Pharmacia) treated with EcoRI and SmaI, were mixed. After addition of a ligation kit (trade name: Mighty Cloning Kit, made by Takara Shuzo) thereto, the mixture was made to react according to the instruction manual. With use of this ligation liquid, *Escherichia coli* JM109 was transformed by the calcium chloride method (Journal of Molecular Biology., vol. 53, 159 (1970)) and was applied to L agar medium (the ingredient composition is the same as that of the above L medium except that L agar medium has 1.5% (w/v) of agar) containing 50 µg/mL of ampicillin, 200 µg/mL of X-gal (5-bromo-4-chloro-3-indoxyl-beta-D-galactopyranoside), and 100 µg/mL of IPTG (isopropyl 1-thio-beta-d-galactoside). A white growing strain on the culture medium was subjected to liquid culture in the usual manner. A plasmid having an about 1.4-kb inserted DNA fragment comprising the xylA gene was extracted from the culture medium with use of a plasmid extraction kit (trade name: QIAprep Spin Miniprep Kit, made by QIAGEN).

The plasmid comprising the xylA gene was named pCRA801.

The about 1.6-kb amplification product treated with the restriction enzymes EcoRI and SmaI was also ligated to the vector pTrc99A treated with EcoRI and SmaI in the same manner to construct a plasmid pCRA802 comprising the xylB gene.

PCR was performed under the same conditions as above except that the constructed pCRA801 as a template, the DNA fragment comprising the xylA gene ligated to the trc promoter (Ptrc), and the primer set shown below were used.

Primer Set for Ptrc-xylA Gene Amplification

```
                                            (SEQ ID NO: 7)
    Primer 5:   5'-CTCTAGATCTCCGACATCATAACGGTTCTG-3'

(SEQ ID NO: 8)
    Primer 6:   5'-CTCTGGATCCCTTCTCTCATCCGCCAAAAC-3'
```

The about 1.6-kb amplification product treated with the restriction enzymes BglII and BamHI was also ligated to the vector coryneform bacterium-*Escherichia coli* shuttle vector pCRB1 (JP 2006-124440 A) treated with the restriction enzymes BglII and BamHI in the same manner to construct a plasmid pCRA810 comprising the Ptrc-xylA gene.

PCR was performed under the same conditions as above except that the constructed pCRA802 as a template, the DNA fragment comprising the xylB gene ligated to the trc promotor (Ptrc), and the primer set shown below were used.

Primer Set for Ptrc-xylB Gene Amplification

```
                                            (SEQ ID NO: 9)
    Primer 6:   5'-CTCTGGATCCCTTCTCTCATCCGCCAAAAC-3'

(SEQ ID NO: 10)
    Primer 7:   5'-CTCTTGATCACCGACATCATAACGGTTCTG-3'
```

The about 1.7-kb amplification product treated with the restriction enzymes FbaI and BamHI was also ligated to the vector pCRA810 treated with FbaI and BamHI in the same manner except that chloramphenicol was used instead of ampicillin, to construct a plasmid pCRA811 (vector pCRA811) comprising the Ptrc-xylB gene (FIG. 1).

(2) Isolation of ara operon and araE from *Corynebacterium Glutamicum* ATCC31831 a) Extraction of Chromosomal DNA from *Corynebacterium Glutamicum* ATCC31831

The extraction of chromosomal DNA from *Corynebacterium glutamicum* ATCC31831 was performed under the same conditions as in the above case of *Escherichia coli* JM109 except that the A liquid medium shown in Table 1 was used and that the culture temperature was 30° C.

TABLE 1

| Composition of A liquid medium (1 L) | Amount (g) |
|---|---|
| Glucose | 40 |
| $(NH_4)_2SO_4$ | 7 |
| Casamino acid | 7 |
| Yeast extract | 2 |
| Urea | 2 |
| $KH_2PO_4$ | 0.5 |
| $K_2HPO_4$ | 0.5 |
| $MgSO_4 \cdot 7H_2O$ | 0.5 |
| $FeSO_4 \cdot 7H_2O$ | 0.006 |
| $MnSO_4 \cdot 7H_2O$ | 0.0042 |
| Thiamine hydrochloride | 0.0002 |
| Biotin | 0.0002 | b) Cloning of L-Arabinose Metabolism-Related Gene from *Corynebacterium Glutamicum* ATCC31831

Cloning of L-arabinose metabolic gene from *Corynebacterium glutamicum* ATCC31831, which had favorably proliferated with use of L-arabinose as a single carbon source, was attempted. Results of homology search in database showed that, among the genes araA, araB, and araD, which encode three kinds of L-arabinose metabolic enzymes, that is, L-arabinose isomerase, L-ribulokinase, and L-ribulose-5-phosphate-4-epimerase, respectively, the gene most highly conserved between species was araA. Then, the following set of primers was synthesized from the conserved sequence in the araA with use of "394 DNA/RNA synthesizer" made by Applied Biosystems, and was used for PCR.

Primer Set for Amplification of araA Homologous Region

```
                                            (SEQ ID NO: 11)
    primer 1 araA:   5'-GGIGAYAMIATGMGIIAIGTIGCIGTIAC-3'

(SEQ ID NO: 12)
    primer 2 araA:   5'-GTYTTCCARTCICCYTC-3'
```

As template DNA, the chromosomal DNA extracted from *Corynebacterium glutamicum* 31831 in the above Example 1 (2) a) was used. PCR was performed with use of "DNA thermal cycler" made by PerkinElmer Cetus and DNA polymerase (trade name: Takara LA Taq HS DNA polymerase, made by Takara Shuzo) as a reaction reagent under the conditions described below.

Reaction Mixture:
(10×) PCR buffer soln.: 5 µL
2.5 mM dNTP Mix: 8 µL
Template DNA: 5 µL (DNA content: 1 µg or less)
The above 2 primers: 0.5 µL each (final conc.: 0.25 µM)
Takara LA Taq HS DNA polymerase: 0.5 µL
DMSO: 5 µL (final conc.: 10%)
Sterile distilled water: 26 µL The above ingredients were mixed, and 50 µL of the reaction mixture was subjected to PCR.

PCR Cycle:
Denaturation step: 94° C., 1 minute
Annealing step: 37° C., 1 minute
Extension step: 72° C., 1 minute A cycle consisting of the above 3 steps was repeated 30 times.

With use of the thus obtained reaction mixture, 1% (w/v) agarose gel electrophoresis was performed, and an about 390-kb DNA fragment comprising an araA-homologous region was detected.

The PCR amplification product was made to react with use of pGEM-T easy vector system (made by Promega) according to the instruction manual.

With use of this ligation liquid, and in the same manner and under the same conditions as in the above Example 1 (1) b), a plasmid having an about 390-bp inserted DNA fragment comprising the araA homologous region was obtained. The DNA sequence was determined by sequencing the plasmid produced in this way. The thus obtained sequence had very high homology with the reported base sequences of other bacterial araAs.

Figure 2:
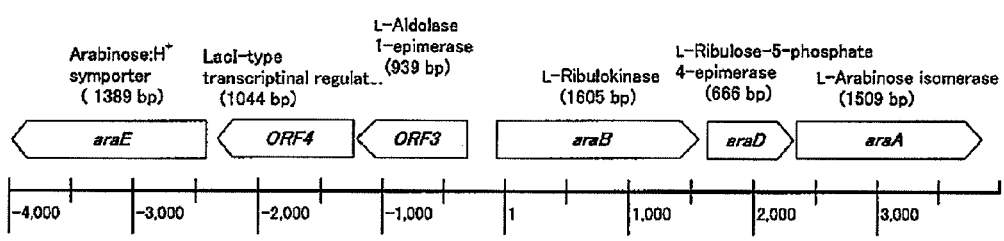
FIG. 2 shows an ara gene map of *Corynebacterium glutamicum* ATCC31831.

As a result of Southern hybridization with use of the probe prepared from the determined sequence and the chromosomal DNA of *Corynebacterium glutamicum* ATCC31831 extracted in the above Example 1 (2) a), in the case of treatment with the restriction enzyme XbaI, a single band was detected at the position of about 9.9 kb. Based on the results of Southern hybridization, colony hybridization was performed to prepare a plasmid ligated with the XbaI fragment comprising araA. The DNA sequence of the plasmid was determined by sequencing the plasmid. Analysis of the obtained sequence confirmed an about 4.0-kb DNA sequence of araB, araD, and araA linked in the order. Also, about 2.5-kb upstream of the araB gene, there was an L-arabinose transport system proton symporter gene, araE (SEQ ID NO: 13) (FIG. 2).

c) Cloning of L-Arabinose Transport System Proton Symporter Gene (araE) Derived from *Corynebacterium Glutamicum* ATCC31831

A DNA fragment comprising the araE gene from *Corynebacterium glutamicum* ATCC31831 was amplified by the PCR method as described below.

In the PCR, the following set of primers was synthesized with use of "394 DNA/RNA Synthesizer" made by Applied Biosystems, and was used.

Primer Set for araE Gene Amplification

```
araE(EcoRI)-Fw:
                                    (SEQ ID NO: 14)
5'-CTCTGAATTCCGGCCAATCGAAGGAGTAAT-3' araE(EcoRI)-Rv:
                                    (SEQ ID NO: 15)
5'-CTCTGAATTCAGGCTAAGGAGTGTTTAAGA-3'
```

Each primer has one EcoRI site added to the end thereof.

As template DNA, the chromosomal DNA extracted from *Corynebacterium glutamicum* ATCC31831 in the above Example 1 (2) a) was used. PCR was performed with use of "DNA thermal cycler" made by PerkinElmer Cetus and DNA polymerase (trade name: Pyrobest DNA polymerase, made by Takara Shuzo) as a reaction reagent under the conditions described below.

Reaction mixture:
(10×) PCR buffer soln.: 10 μL
2.5 mM dNTP Mix: 8 μL
Template DNA: 2 μL (DNA content: 500 ng or less)
The above 2 primers: 0.5 μL each (final conc.: 0.2 μM)
Pyrobest DNA polymerase: 0.5 μL
Sterile distilled water: 79 μL The above ingredients were mixed, and 100 μL of the reaction mixture was subjected to PCR.

PCR Cycle:
Denaturation step: 98° C., 10 seconds
Annealing step: 55° C., 30 seconds
Extension step: 72° C., 2 minutes A cycle consisting of the above 3 steps was repeated 30 times.

With use of the thus obtained reaction mixture, 1% (w/v) agarose gel electrophoresis was performed, and an about 1.7-kb DNA fragment comprising the araE gene was detected.

The amplification products treated with the above-mentioned restriction enzyme EcoRI and pKK223-3 (made by Pharmacia) treated with EcoRI were mixed. After addition of Mighty Cloning Kit (made by Takara Shuzo) thereto, the mixture was made to react according to the instruction manual.

With use of this ligation liquid, *Escherichia coli* JM109 was transformed by the calcium chloride method and was applied to L agar medium (the ingredient composition is the same as that of the above L medium except that L agar medium has 1.5% (w/v) of agar) containing 50 μg/mL of ampicillin.

A growing strain on the culture medium was subjected to liquid culture in the usual manner. A plasmid having an about 1.7-kb inserted DNA fragment comprising the araE gene was extracted from the culture medium with use of QIAprep Spin Miniprep Kit (made by QIAGEN).

Figure 3:
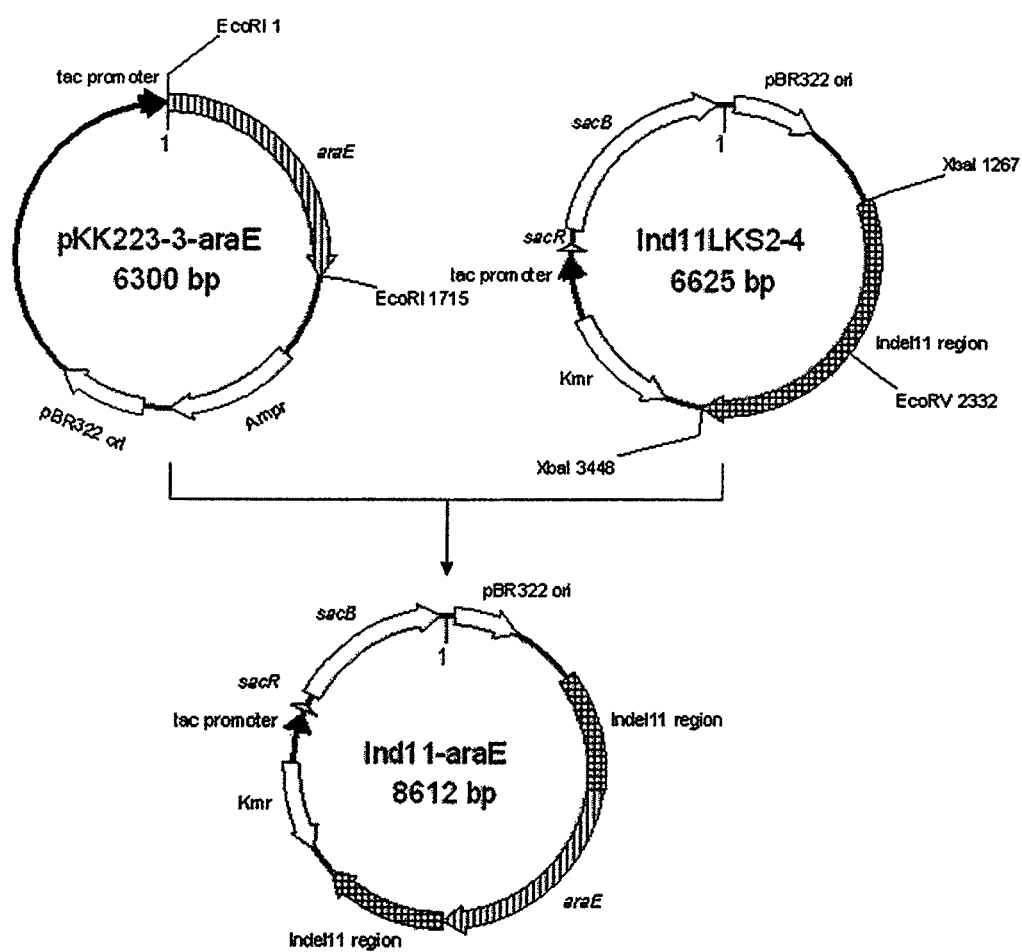
FIG. 3 is a schematic view showing a method for preparing the vector Ind11-araE prepared in Example 1 (3).

The plasmid comprising the araE gene was named pKK223-3-araE (FIG. 3).

(3) Construction of Vector Ind-araE for Markerless Integration of araE

Next, DNA region necessary for markerless integration of the araE gene into the chromosome of *Corynebacterium glutamicum* R was determined based on the sequences reported to be nonessential for *Corynebacterium glutamicum* R to grow (Appl. Environ. Microbiol. Vol. 71, 3369-3372 (2005)) (SSIs). The DNA region (Indel11) was amplified by the PCR method as described below.

In the PCR, the following set of primers was synthesized with use of "394 DNA/RNA Synthesizer" made by Applied Biosystems, and was used.

Primer set for Amplifying Indel11 for integrating the araE gene

```
Indel11(XbaI)-Fw1:
                                    (SEQ ID NO: 16)
5'-CTCTTCTAGACCTCAATAGAGTCTTCAGAT-3'

Indel11(XbaI)-Rv1:
                                    (SEQ ID NO: 17)
5'-CTCTTCTAGATGCTCAGTATGAATGGCCTT-3'
```

Each primer has one XbaI site added to the end thereof.

As template DNA, the chromosomal DNA extracted from *Corynebacterium glutamicum* R in the same manner as in the above Example 1 (2) a) was used. PCR was performed under the same conditions as in the above Example 1 (2) b) except that Takara LA Taq HS DNA polymerase was used, that DMSO was not contained in the reaction mixture, and that PCR cycle was as follows.

PCR Cycle:
Denaturation step: 94° C., 30 seconds
Annealing step: 55° C., 30 seconds
Extension step: 72° C., 3 minutes A cycle consisting of the above 3 steps was repeated 30 times.

With use of the thus obtained reaction mixture, 1% (w/v) agarose gel electrophoresis was performed, and an about 2.0-kb DNA fragment comprising Indel11 was detected.

The amplification product treated with the above-mentioned restriction enzyme XbaI and the plasmid for markerless gene disruption, pCRA725, treated with XbaI (J. Mol. Microbiol. Biotechnol., Vol. 8, 243-254 (2004); and JP 2006-124440 A) were mixed. After addition of Mighty Cloning Kit (made by Takara Shuzo) thereto, the mixture was made to react according to the instruction manual.

With use of this ligation liquid, and in the same manner and under the same conditions as in the above Example 1 (1) b) except that 50 μg/mL of kanamycin was used instead of chloramphenicol as the antibacterial agent used in the medium for transformant selection, a plasmid having an about 2.0-kb inserted DNA fragment comprising the Indel11 region was obtained.

The plasmid comprising the Indel11 for integrating the araE gene was named Ind11LKS2-4 (FIG. 3).

The plasmid pKK223-3-araE was digested with EcoRI and the digest was separated by agarose gel electrophoresis. Then, about 2.0-kb DNA fragments comprising the gene from the gel were collected with use of MinElute Gel Extraction Kit (made by QIAGEN). The obtained DNA was blunt-ended with a blunting kit (trade name: DNA Blunting Kit, made by Takara Shuzo) and mixed with Ind11LKS2-4 treated with the restriction enzyme EcoRV. After addition of Mighty Cloning Kit (made by Takara Shuzo) thereto, the mixture was made to react according to the instruction manual.

With use of this ligation liquid, *Escherichia coli* JM109 was transformed by the calcium chloride method and was applied to L agar medium (the ingredient composition is the same as that of the above L medium except that L agar medium has 1.5% (w/v) of agar) containing 50 μg/mL of kanamycin.

A growing strain on the culture medium was subjected to liquid culture in the usual manner. A plasmid having an about 1.7-kb inserted DNA fragment comprising the araE gene was extracted from the culture medium with use of QIAprep Spin Miniprep Kit (made by QIAGEN).

The plasmid for integrating the araE gene was named Ind11-araE (FIG. 3).

(4) Preparation of *Corynebacterium glutamicum* Ind-araE

The plasmid Ind11-araE for integrating the araE gene is a plasmid non-replicable in *Corynebacterium glutamicum* R. Ind11-araE was transferred into *Corynebacterium glutamicum* R according to the electric pulse method (Agric. Biol. Chem., Vol. 54, 443-447 (1990); and Res. Microbiol., Vol. 144 and 181-185 (1993)) and the strain was applied to A agar medium (the ingredient composition is the same as that of the above A liquid medium except that A agar medium has 1.5% (w/v) of agar) containing 50 μg/mL of kanamycin.

In addition, the strain obtained in the above culture medium was applied to ET agar medium (the ingredient composition is the same as that of BT liquid medium shown in Table 2 except that BT agar medium has 1.5% (w/v) of agar) containing 10% (w/v) of sucrose.

TABLE 2

| Composition of BT liquid medium (1 L) | Amount (g) |
|---|---|
| $(NH_4)_2SO_4$ | 7 |
| Urea | 2 |
| $KH_2PO_4$ | 0.5 |
| $K_2HPO_4$ | 0.5 |
| $MgSO_4 \cdot 7H_2O$ | 0.5 |
| $FeSO_4 \cdot 7H_2O$ | 0.006 |
| $MnSO_4 \cdot 7H_2O$ | 0.0042 |
| Thiamine hydrochloride | 0.0002 |
| Biotin | 0.0002 |

In the case where 1-site homologous recombination has occurred between the plasmid Ind11-araE and the homologous region of the chromosome, the strain shows kanamycin resistance due to expression of the kanamycin-resistant gene on Ind11-araE but lacks growing ability in sucrose due to expression of the sacR-sacB gene of *Bacillus subtilis*. In the case where 2-site homologous recombination has occurred between the plasmid Ind11-araE and the homologous region of the chromosome, the strain shows kanamycin sensitivity due to deletion of the kanamycin-resistant gene from Ind11-araE and growing ability in culture medium containing sucrose due to deletion of the sacR-sacB gene from Ind11-araE. Therefore, the target strain having an araE gene integrated into the chromosome shows kanamycin sensitivity and growing ability in culture medium containing sucrose.

The strain having kanamycin sensitivity and growing ability in culture medium containing sucrose was named *Corynebacterium glutamicum* Ind-araE.

(5) Construction of *Corynebacterium glutamicum* R/pCRA811 and *Corynebacterium glutamicum* Ind-araE/pCRA811

The plasmid pCRA811 was separately transferred into *Corynebacterium glutamicum* R and *Corynebacterium glutamicum* Ind11-araE according to the electric pulse method mentioned in the above Example 1 (4). With use of A agar medium (the ingredient composition is the same as that of the above A liquid medium except that A agar medium has 1.5% (w/v) of agar) containing 5 μg/mL of chloramphenicol, transformed strains, that is, *Corynebacterium glutamicum* R/pCRA811 and *Corynebacterium glutamicum* Ind-araE/pCRA811, were obtained. *Corynebacterium glutamicum* Ind-araE/pCRA811 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-576 on May 28, 2008.

Example 2

Aerobic Culture of *Corynebacterium Glutamicum* R/pCRA811 and *Corynebacterium Glutamicum* Ind-araE/pCRA811 in a Culture Medium Containing D-Xylose as a Single Carbon Source

Figure 4:
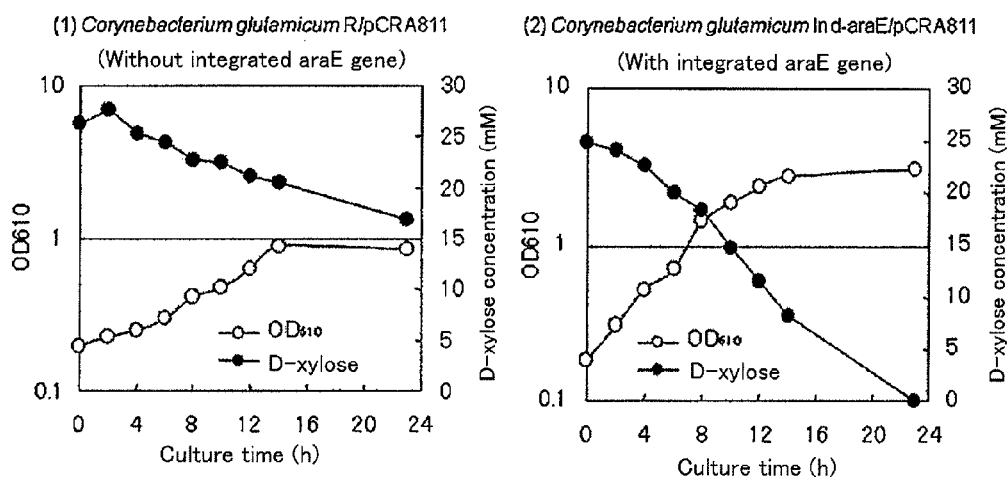
FIG. 4 shows the time course of D-xylose consumption by and proliferation of *Corynebacterium glutamicum* R/pCRA811 (FIG. 4 (1)) and *Corynebacterium glutamicum* Ind-araE/pCRA811 (FIG. 4 (2)) during culture under aerobic conditions in BT culture medium containing D-xylose as a single carbon source.

*Corynebacterium glutamicum* R/pCRA811 and *Corynebacterium glutamicum* Ind-araE/pCRA811 both prepared in the above Example 1 (5) were separately used for investigation of decrease in D-xylose and of cell proliferation in BT liquid medium containing D-xylose as a single carbon source. An inoculation loop of each of the two strains was inoculated in a separate test tube containing 10 mL of a medium having the same ingredient composition as that of A liquid medium except that it further contains 5 μg/mL of chloramphenicol, and aerobically cultured at 200 rpm at 33° C. for 13 hours. After washed with the BT culture medium twice, the strain was inoculated in 100 mL of BT culture medium containing 25 mM of D-xylose as a single carbon source so that the OD610 became 0.2. The concentration of D-xylose was repeatedly checked by sampling a small amount of the culture medium and analyzing it by liquid chromatography for change in consumption over time. The results are shown in FIGS. 4 (1) and (2). In FIGS. 4 (1) and (2), white circles show the change in OD610 and black circles show the change in the concentration of D-xylose in the culture medium. FIG. 4 (1) shows the time course of D-xylose consumption by and proliferation of *Corynebacterium glutamicum* R/pCRA811 not having a transferred araE gene therein. FIG. 4 (2) shows the time course of D-xylose consumption by and proliferation of *Corynebacterium glutamicum* Ind-araE/pCRA811 having an araE gene integrated into the chromosome. As shown in FIGS. 4 (1) and (2), under aerobic conditions, the consumption rate of D-xylose by and proliferation rate of *Corynebacterium glutamicum* Ind-araE/pCRA811 having an araE integrated into the chromosome (FIG. 4 (2)) were significantly increased as compared with those by *Corynebacterium glutamicum* R/pCRA811 not having a transferred araE gene therein (FIG. 4 (1)).

Example 3

Sugar Consumption and Lactic Acid Production by *Corynebacterium Glutamicum* R/pCRA811 and *Corynebacterium Glutamicum* Ind-araE/pCRA811 Using D-Xylose as a Single Substrate Under Reducing Conditions (1) Aerobic Culture Proliferation

*Corynebacterium glutamicum* R/pCRA811 and *Corynebacterium glutamicum* Ind-araE/pCRA811 prepared in Example 1 (5) and stored at −80° C. in a freezer were separately applied to A agar medium for plate culture (the ingredient composition is the same as that of the above A liquid medium except that A agar medium has 1.5% (w/v) of agar) containing 5 µg/mL of chloramphenicol, and left stand in the dark at 33° C. for 12 hours.

An inoculation loop of each of the two kinds of *Corynebacterium* strains each grown on a plate as above was inoculated in a separate test tube containing 10 mL of A liquid medium containing 5 µg/mL of chloramphenicol, and aerobically cultured at 200 rpm at 33° C. for 12 hours.

The two kinds of *Corynebacterium* strains each grown under the above conditions were each transferred into a 1-L conical flask containing 500 mL of A liquid medium containing 5 µg/mL of chloramphenicol, which is a medium for aerobic culture, and aerobically cultured at 200 rpm at 33° C. for 12 hours. Bacterial cells cultured and proliferated as above were collected by centrifugation (5,000×g at 4° C. for 10 minutes) and subjected to the next lactic acid producing reaction under reducing conditions.

(2) Sugar Consumption and Organic Acid Generation Under Reducing Conditions 4 g of each of the two kinds of wet cells (about 0.8 g in terms of dry cells) collected in the step of aerobic culture proliferation in Example 3 (1) was separately suspended in 80 mL of BT-U culture medium (the ingredient composition is the same as that of the above BT liquid medium except that the BT-U medium does not contain urea), and placed in a 100-mL vial. After addition of 100 mM of D-xylose as a carbon source and 100 mM of sodium hydrogen carbonate, the mixture was gently stirred in a sealed condition at 33° C. for lactic acid producing reaction under reducing conditions.

During the reaction, the pH in the reactor was kept at 7.5 with a 2.5N (normality) $NH_4OH$ aqueous solution (2.5N aqueous ammonia solution).

The concentrations of D-xylose and lactic acid in the reactor were repeatedly checked by sampling a small amount of the culture medium and analyzing it by liquid chromatography for changes in consumption and production over time.

Figure 5:
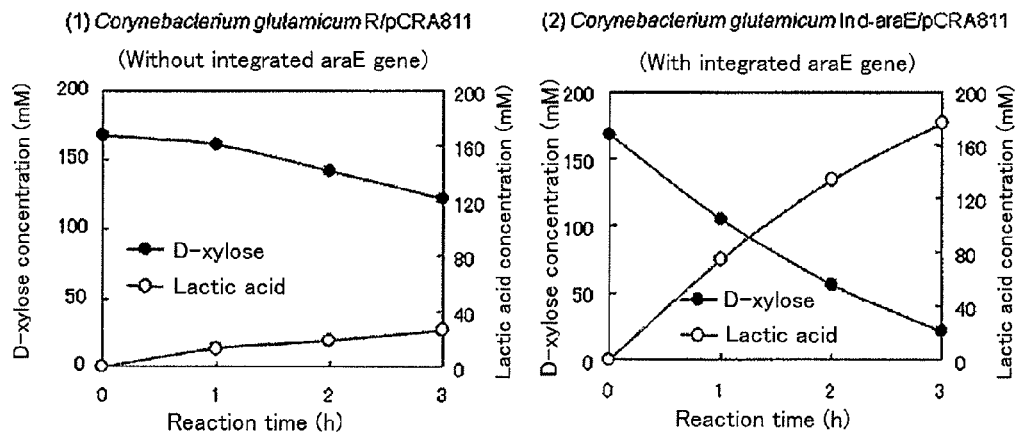
FIG. 5 shows the time course of D-xylose consumption and lactic acid production by *Corynebacterium glutamicum* R/pCRA811 (FIG. 5 (1)) and *Corynebacterium glutamicum* Ind-araE/pCRA811 (FIG. 5 (2)) under reducing conditions with use of D-xylose as a single substrate.

The results are shown in FIGS. 5 (1) and (2). FIG. 5 (1) shows the time course of D-xylose consumption and lactic acid production by *Corynebacterium glutamicum* R/pCRA811 not having a transferred araE gene therein. FIG. 5 (2) shows the time course of D-xylose consumption and lactic acid production by *Corynebacterium glutamicum* Ind-araE/pCRA811 having an araE gene integrated into the chromosome. In FIGS. 5 (1) and (2), black circles show the change in the concentration of D-xylose and white circles show the change in the concentration of lactic acid in the culture medium.

The rates of D-xylose consumption and lactic acid production mean hourly amounts of consumption and production from 0 to 3 hours after the start of the reaction, respectively. The D-xylose consumption rate and the lactic acid production rate by *Corynebacterium glutamicum* R/pCRA811 (FIG. 5 (1)) were 15.1 mM/h and 18.5 mM/h, respectively while the D-xylose consumption rate and the lactic acid production rate by *Corynebacterium glutamicum* Ind-araE/pCRA811 (FIG. 5 (2)) were 48.4 mM/h and 58.5 mM/h, respectively.

The results show that, even under reducing conditions, the D-xylose consumption rate and the lactic acid production rate by *Corynebacterium glutamicum* Ind-araE/pCRA811 having an araE gene integrated into the chromosome were significantly increased as compared with those by *Corynebacterium glutamicum* R/pCRA811 not having a transferred araE gene therein.

Example 4

Aerobic Culture of *Corynebacterium Glutamicum* R/pCRA811 and *Corynebacterium Glutamicum* Ind-araE/pCRA811 in a Culture Medium Containing Mixed Sugar of D-Glucose and D-Xylose as Carbon Sources Aerobic culture proliferation of and sugar consumption by *Corynebacterium glutamicum* R/pCRA811 and *Corynebacterium glutamicum* Ind-araE/pCRA811 were investigated under the same conditions and in the same manner as in the above Example 2 except that a mixture of D-glucose and D-xylose (3.6 g/L and 3.6 g/L, respectively; the ratio was 1:1) was used instead of D-xylose as the carbon source.

Figure 6:
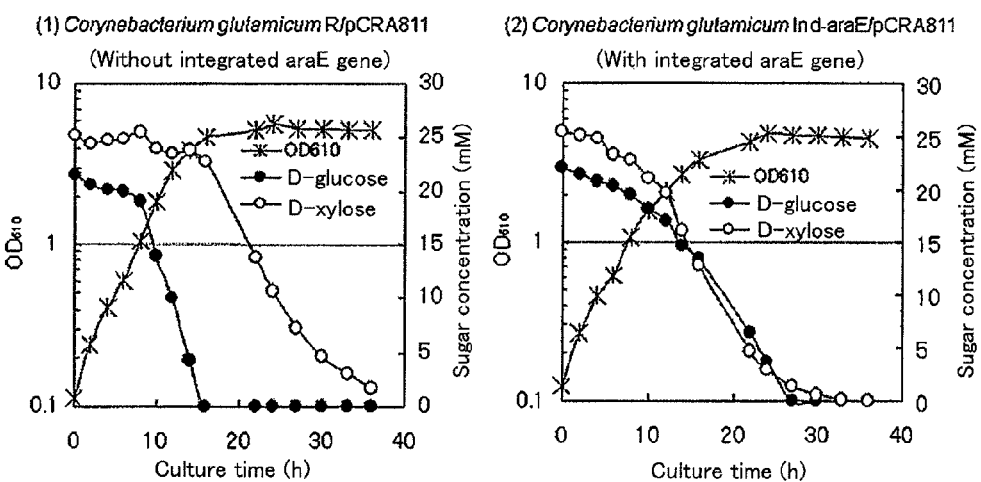
FIG. 6 shows the time course of D-glucose and D-xylose consumption by and proliferation of *Corynebacterium glutamicum* R/pCRA811 (FIG. 6 (1)) and *Corynebacterium glutamicum* Ind-araE/pCRA811 (FIG. 6 (2)) during culture under aerobic conditions in BT culture medium containing D-glucose and D-xylose as carbon sources.

The results are shown in FIGS. 6 (1) and (2). FIG. 6 (1) shows the time course of D-glucose and D-xylose consumption by and proliferation of *Corynebacterium glutamicum* R/pCRA811 not having a transferred araE gene therein. FIG. 6 (2) shows the time course of D-glucose and D-xylose consumption by and proliferation of *Corynebacterium glutamicum* Ind-araE/pCRA811 having an araE gene integrated into the chromosome. In FIGS. 6 (1) and (2), asterisks show the change in OD610. Black circles show the change in the concentration of D-glucose in the culture medium. White circles show the change in the concentration of D-xylose in the culture medium.

As shown in FIGS. 6 (1) and (2), under aerobic conditions, the consumption rate of D-xylose by *Corynebacterium glutamicum* Ind-araE/pCRA811 having an araE integrated into the chromosome (FIG. 6 (2)) was significantly increased as compared with that by *Corynebacterium glutamicum* R/pCRA811 not having a transferred araE gene therein (FIG. 6 (1)). While *Corynebacterium glutamicum* Ind-araE/pCRA811 completely consumed the D-glucose and D-xylose in the culture medium within 30 hours, *Corynebacterium glutamicum* R/pCRA811 did not, and after a lapse of the same 30 hours, remaining D-xylose was observed.

Further, in aerobic culture, while *Corynebacterium glutamicum* R/pCRA811 showed glucose repression in D-xylose utilization in the presence of both D-glucose and D-xylose, *Corynebacterium glutamicum* Ind-araE/pCRA811 was capable of simultaneous parallel utilization of D-glucose and D-xylose.

Example 5

Sugar Consumption and Lactic Acid Production by *Corynebacterium Glutamicum* R/pCRA811 and *Corynebacterium Glutamicum* Ind-araE/pCRA811 Using Mixed Sugar of D-Glucose and D-Xylose as a Substrate Under Reducing Conditions The proliferation by aerobic culture and the subsequent reaction under reducing conditions were performed in the same manner and under the same conditions as in the above Example 3 except that a mixture of D-glucose and D-xylose (40 g/L and 20 g/L, respectively; the ratio was about 2:1) was used instead of D-xylose as the substrate.

Figure 7:
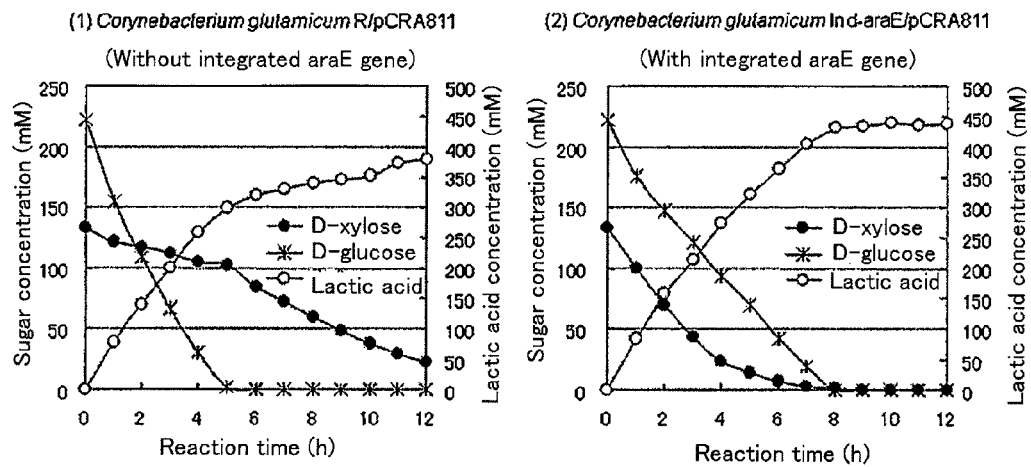
FIG. 7 shows the time course of D-glucose and D-xylose consumption and lactic acid production by *Corynebacterium glutamicum* R/pCRA811 (FIG. 7 (1)) and *Corynebacterium glutamicum* Ind-araE/pCRA811 (FIG. 7 (2)) under reducing conditions with use of mixed sugar of D-glucose and D-xylose (2:1).

The results are shown in FIGS. 7 (1) and (2). FIG. 7 (1) shows the time course of D-glucose and D-xylose consumption and lactic acid production by *Corynebacterium glutamicum* R/pCRA811 not having a transferred araE gene therein. FIG. 7 (2) shows the time course of D-glucose and D-xylose consumption and lactic acid production by *Corynebacterium glutamicum* Ind-araE/pCRA811 having an araE gene integrated into the chromosome. In FIGS. 7 (1) and (2), black circles show the change in the concentration of xylose in the culture medium. Asterisks show the change in the concentration of D-glucose in the culture medium. White circles show the change in the concentration of lactic acid in the culture medium.

As shown in FIGS. 7 (1) and (2), even under reducing conditions, the consumption rate of D-xylose by *Corynebacterium glutamicum* Ind-araE/pCRA811 having an araE integrated into the chromosome (FIG. 7 (2)) was significantly increased as compared with that by *Corynebacterium glutamicum* R/pCRA811 not having a transferred araE gene therein (FIG. 7 (1)). While *Corynebacterium glutamicum* Ind-araE/pCRA811 completely consumed the D-glucose and D-xylose within 8 hours, *Corynebacterium* glutamicumR/pCRA811 did not, and after a lapse of the same 8 hours, a significant amount of remaining D-xylose was observed. The concentrations of lactic acid production by *Corynebacterium glutamicum* R/pCRA811 and *Corynebacterium glutamicum* Ind-araE/pCRA811 after 8 hours were 339 mM and 431 mM, respectively, where the latter was about 1.3 times higher than the former.

Further, under reducing conditions, while *Corynebacterium glutamicum* R/pCRA811 showed glucose repression in D-xylose utilization in the presence of both D-glucose and D-xylose, *Corynebacterium glutamicum* Ind-araE/pCRA811 was capable of simultaneous parallel utilization of D-glucose and D-xylose.

Example 6

Construction of *Corynebacterium Glutamicum* X5/Plac-araBAD and *Corynebacterium Glutamicum* X5-Ind-araE/Plac-araBAD (1) Method for Construction of Plac-araBAD The three genes of *Escherichia coli*, an L-arabinose isomerase gene (hereinafter referred to as araA), an L-ribulokinase gene (hereinafter referred to as araB), and an L-ribulose-5-phosphate-4-epimerase gene (hereinafter referred to as araD), form an operon (araBAD) where araB, araA and araD are linked in the order (SEQ ID NO: 18) (Gene, Vol. 47, 231-244 (1986)). A DNA fragment comprising the araBAD gene was amplified by the PCR method as described below. In the PCR, the following set of primers was synthesized based on the sequence of *Escherichia coli* with use of "394 DNA/RNA Synthesizer" made by Applied Biosystems for cloning of the araBAD, and was used.

Primer Set for araBAD Gene Amplification

Eco_ara_fw4_EcoI: 5'-
CTCT<u>GAATTC</u>ACCCGTTTTTTTGGATGGAG -3' (SEQ ID NO: 19)
Eco_ara_Rv2_Sal: 5'-
CTCT<u>GTCGAC</u>GCCAGTGTCGGGTTAAGATA -3' (SEQ ID NO: 20)

The former and the latter have an EcoRI site and a SalI site added to the end thereof, respectively.

The chromosomal DNA of the *Escherichia coli* JM109 extracted in the above Example 1 (1) a) was used as template DNA.

PCR was performed with use of "DNA thermal cycler" made by PerkinElmer Cetus and DNA polymerase (trade name: PrimeSTAR HS DNA polymerase, made by Takara Shuzo) as a reaction reagent under the conditions described below.

Reaction Mixture:

(5×) PCR buffer soln.: 10 μL
2.5 mM dNTP Mix: 4 μL
Template DNA: 1 μL (DNA content: 200 ng or less)
The above 2 primers: 1 μL each (final conc.: 0.2 μM)
PrimeSTAR HS DNA polymerase: 0.5 μL
Sterile distilled water: 33.5 μL The above ingredients were mixed, and 50 μL of the reaction mixture was subjected to PCR.

PCR cycle:

Denaturation step: 98° C., 10 seconds
Annealing step: 55° C., 10 seconds
Extension step: 72° C., 5 minutes A cycle consisting of the above 3 steps was repeated 30 times.

With use of part of the thus obtained reaction mixture, 1% (w/v) agarose gel electrophoresis was performed, and an about 4.5-kb DNA fragment comprising the araBAD gene was detected.

The amplification product treated with the above-mentioned restriction enzymes EcoRI and SalI, and the coryneform bacterium-*Escherichia coli* shuttle vector pCRB1 (JP 2006-124440 A) treated with EcoRI and SalI, were mixed. After addition of a ligation kit (trade name: Mighty Cloning Kit, made by Takara Shuzo) thereto, the mixture was made to react according to the instruction manual.

With use of this ligation liquid, *Escherichia coli* JM109 was transformed by the calcium chloride method (Journal of Molecular Biology., vol. 53, 159 (1970)) and was applied to L agar medium (the ingredient composition is the same as that of the above L medium except that L agar medium has 1.5% (w/v) of agar) containing 50 μg/mL of chloramphenicol, 200 μg/mL of X-gal (5-bromo-4-chloro-3-indoxyl-beta-D-galactopyranoside), and 100 μg/mL of IPTG (isopropyl 1-thio-beta-d-galactoside).

A white growing strain on the culture medium was subjected to liquid culture in the usual manner. A plasmid having an about 4.5-kb inserted DNA fragment comprising the araBAD gene was extracted from the culture medium with use of a plasmid extraction kit (trade name: QIAprep Spin Miniprep Kit, made by QIAGEN).

Figure 8:
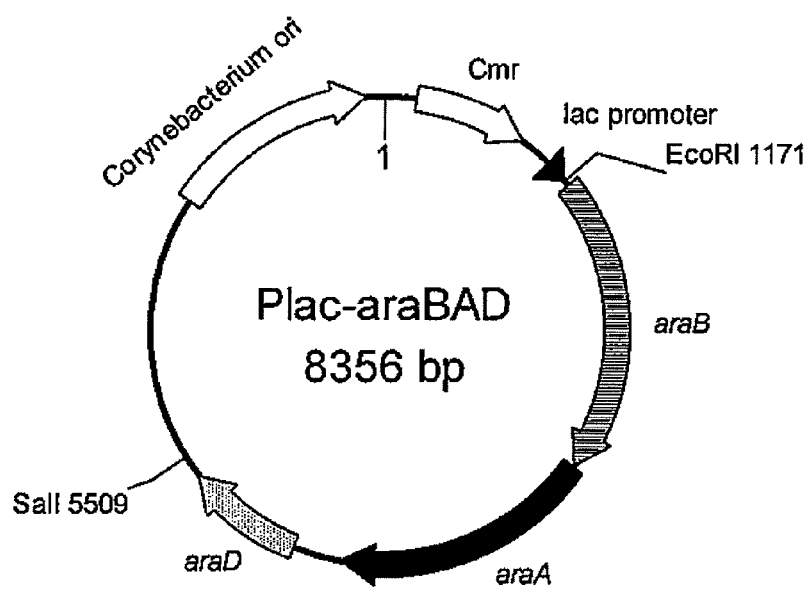
FIG. 8 is a schematic view showing the vector Plac-araBAD prepared in Example 6 (1).

The plasmid comprising the araBAD gene was named Plac-araBAD (FIG. 8).

(2) Method for Construction of *Corynebacterium Glutamicum* X5 and *Corynebacterium Glutamicum* X5-IndaraE a) Cloning of SSI Region from *Corynebacterium Glutamicum* R In order to integrate D-xylose metabolism-related genes xylA and xylB into the SSI region of *Corynebacterium glutamicum* R, the DNA region was amplified by the PCR method with use of the primers shown in Table 3 and the chromosomal DNA of *Corynebacterium glutamicum* R. PCR was performed under the same conditions as in the above Example 1 (3) with use of Takara LA Taq HS DNA polymerase.

With use of the reaction mixture obtained above, 1% (w/v) agarose gel electrophoresis was performed, and an about 2.0 to 3.0-kb DNA fragment was detected.

The amplification product treated with the restriction enzyme shown in Table 3 and the plasmid for markerless gene disruption, pCRA725, treated with the same restriction enzyme (J. Mol. Microbiol. Biotechnol., Vol. 8, 243-254 (2004); and JP 2006-124440 A) were mixed. After addition of Mighty Cloning Kit (made by Takara Shuzo) thereto, the mixture was made to react according to the instruction manual.

With use of this ligation liquid, and in the same manner and under the same conditions as in the above Example 6 (1) except that 50 µg/mL of kanamycin was used instead of chloramphenicol as the antibacterial agent used in the medium for transformant selection, a plasmid having an about 2.0- to 3.0-kb inserted DNA fragment comprising corresponding SSI region was obtained.

In Table 3, an [a]asterisk means that the primer is for inverse PCR.

In Table 3, an underlined base sequence is a restriction enzyme site prepared for cloning.

b) Construction of Vector for Markerless Transfer of xylA-xylB Gene

The plasmid pCRA811 prepared in the above Example 1 (1) was treated with XbaI and XhoI, and the resulting fragments were separated by agarose gel electrophoresis. Then, about 3.3-kb DNA fragments comprising the xylA-xylB gene from the gel were collected with use of MinElute Gel Extraction Kit (made by QIAGEN). The obtained DNA was mixed with the plasmid prepared in the above Example 6 (2) a) and treated with restriction enzymes XbaI and XhoI. After addition of Mighty Cloning Kit (made by Takara Shuzo) thereto, the mixture was made to react according to the instruction manual.

With use of this ligation liquid, *Escherichia coli* JM109 was transformed by the calcium chloride method and was applied to L agar medium (the ingredient composition is the same as that of the above L medium except that L agar medium has 1.5% (w/v) of agar) containing 50 µg/mL of kanamycin.

A growing strain on the culture medium was subjected to liquid culture in the usual manner. A plasmid having an about 3.3-kb inserted DNA fragment comprising the xylA-xylB gene was extracted from the culture medium with use of QIAprep Spin Miniprep Kit (made by QIAGEN).

TABLE 3

Primers for cloning of SSI region

| Primer[a] | SEQ ID No. | Target gene | Sequence (5'-3') | Overhanged restriction site |
|---|---|---|---|---|
| primer 1 | 21 | Xyl3 region | CTCTTCTAGATGATGAAGGTTTCCCCGCCG | XbaI |
| primer 2 | 22 | Xyl3 region | CTCTTCTAGATCGTATACCCCTATGGGGTA | XbaI |
| primer 3* | 23 | Xyl3 region | CTCTTCTAGAGTTCCGCTTCGGAGAGAGAT | XbaI |
| primer 4* | 24 | Xyl3 region | CTCTGAGCTCCACCGTCAGGTGAAATACCT | SacI |
| primer 5 | 25 | Xyl7 region | CTCTGAGCTCTGATTGCACGATGGCGAAAA | SacI |
| primer 6 | 26 | Xyl7 region | CTCTGTCGACCTGCAACAAGTGAAAAAAGA | SalI |
| primer 7* | 27 | Xyl7 region | CTCTTCTAGAGCTGCCGTAGCTTTTTGGGA | XbaI |
| primer 8* | 28 | Xyl7 region | CTCTCTCGAGTACTCACCTTTTCGATCCGC | XhoI |
| primer 9 | 29 | Xyl8 region | CTCTGAGCTCGTGAACATATCGGCATCGAG | SacI |
| primer 10 | 30 | Xyl8 region | CTCTGTCGACCTATGGCGTTCTATACTGCG | SalI |
| primer 11* | 31 | Xyl8 region | CTCTTCTAGATATGCAAGAAGCAAGCAAGT | XbaI |
| primer 12* | 32 | Xyl8 region | CTCTCTCGAGTCTCATAAAAGTTCTCCGAT | XhoI |
| primer 13 | 33 | Xyl4 region | CTCTGAGCTCAGCTGAGAGAAAAGCTTTCG | SacI |
| primer 14 | 34 | Xyl4 region | CTCTGTCGACAGAGACCGTAGAGCTAATCC | SalI |
| primer 15* | 35 | Xyl4 region | CTCTTCTAGAGTCTCTAAACCAAACAGGTG | XbaI |
| primer 16* | 36 | Xyl4 region | CTCTCTCGAGAACCACCGAATAGCGCATGC | XhoI |
| primer 17 | 37 | Xyl1 region | CTCTGTCGACTCCGTGGACAATTTTCATCC | SalI |
| primer 18 | 38 | Xyl1 region | CTCTGCATGCAAGCACACCAATTAGTAATG | SphI | c) Preparation of *Corynebacterium Glutamicum* X5 and *Corynebacterium Glutamicum* X5-Ind-araE The plasmid prepared in the above Examples 6 (2) b) for transferring the xylA-xylB gene was integrated into the SSI region of *Corynebacterium glutamicum* R according to the method of the above Example 1 (4) in the order of Xy13, 7, 8, 4, 1, 11, and 6. The finally obtained strain was named *Corynebacterium glutamicum* X5.

Further, the plasmid prepared in the above Example 1 (3), that is, the plasmid Ind11-araE for transferring the araE gene was transferred into *Corynebacterium glutamicum* X5 according to the same method as above. The obtained strain was named *Corynebacterium glutamicum* X5-Ind-araE.

(3) Construction of *Corynebacterium Glutamicum* X5/Plac-araBAD and *Corynebacterium Glutamicum* X5-Ind-araE/Plac-araBAD The plasmid Plac-araBAD was separately transferred into *Corynebacterium glutamicum* X5 and *Corynebacterium glutamicum* X5-Ind-araE according to the electric pulse method mentioned in the above Example 1 (4). With use of A agar medium (the ingredient composition is the same as that of the above A liquid medium except that A agar medium has 1.5% (w/v) of agar) containing 5 µg/mL of chloramphenicol, transformed strains, that is, *Corynebacterium glutamicum* X5/Plac-araBAD and *Corynebacterium glutamicum* X5-Ind-araE/Plac-araBAD were obtained. *Corynebacterium glutamicum* X5-Ind-araE/Plac-araBAD was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-577 on May 28, 2008.

Example 7

Sugar Consumption and Lactic Acid Production by *Corynebacterium Glutamicum* X5/Plac-araBAD and *Corynebacterium Glutamicum* X5-Ind-araE/Plac-araBAD Using Mixed Sugar of D-Glucose and D-Xylose as a Substrate Under Reducing Conditions In the same manner and under the same conditions as in the above Example 3, each of *Corynebacterium glutamicum* X5/Plac-araBAD and *Corynebacterium glutamicum* X5-Ind-araE/Plac-araBAD was proliferated by aerobic culture. Then, the reaction under reducing conditions was performed in the same manner and under the same conditions as in the above Example 3 except that a mixture of D-glucose, D-xylose, and L-arabinose (32 g/L, 16 g/L, and 6.4 g/L, respectively; the ratio was 5:2.5:1) was used instead of D-xylose as the substrate.

Figure 9:
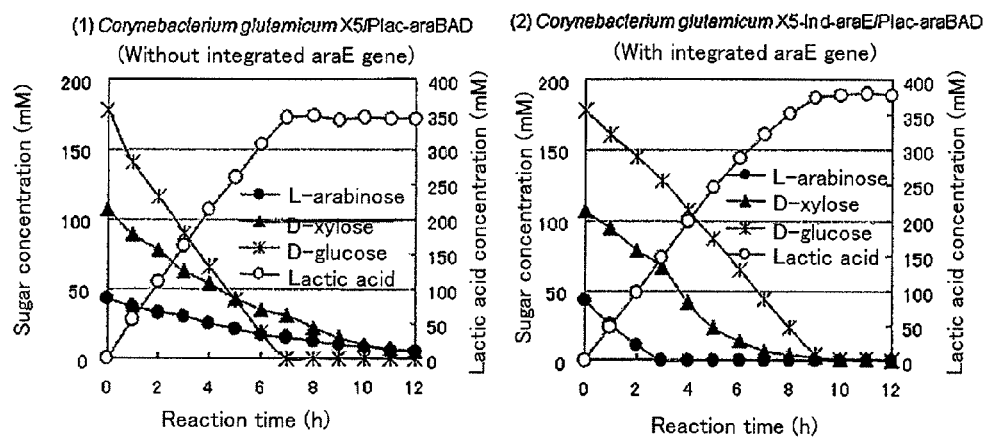
FIGS. 9 (1) and (2) show the time course of sugar consumption and lactic acid production by *Corynebacterium glutamicum* X5/Plac-araBAD (FIG. 9 (1)) and *Corynebacterium glutamicum* X5-Ind-araE/Plac-araBAD (FIG. 9 (2)) under reducing conditions with use of mixed sugar of D-glucose, D-xylose, and L-arabinose (5:2.5:1).

The results are shown in FIGS. 9 (1) and (2). FIG. 9 (1) shows the time course of sugar consumption by *Corynebacterium glutamicum* X5/Plac-araBAD not having a transferred araE gene therein. FIG. 9 (2) shows the time course of sugar consumption by *Corynebacterium glutamicum* X5-Ind-araE/Plac-araBAD having an araE integrated into the chromosome. In FIGS. 9 (1) and (2), black circles show the change in the concentration of L-arabinose in the culture medium. Triangles show the change in the concentration of D-xylose in the culture medium. Asterisks show the change in the concentration of D-glucose in the culture medium. White circles show the change in the concentration of lactic acid in the culture medium.

As shown in FIGS. 9 (1) and (2), under reducing conditions, the consumption rates of D-xylose and L-arabinose by *Corynebacterium glutamicum* X5-Ind-araE/Plac-araBAD having an araE integrated into the chromosome (FIG. 9 (2)) were significantly increased as compared with those by *Corynebacterium glutamicum* X5/Plac-araBAD not having a transferred araE gene therein (FIG. 9 (1)). While *Corynebacterium glutamicum* X5-Ind-araE/Plac-araBAD completely consumed the three kinds of saccharides: D-glucose, D-xylose, and L-arabinose in the culture medium within 9 hours, *Corynebacterium glutamicum* X5/Plac-araBAD did not, and after a lapse of the same 9 hours, remaining D-xylose and L-arabinose were observed. As a result, the concentrations of lactic acid production by *Corynebacterium glutamicum* X5/Plac-araBAD and *Corynebacterium glutamicum* X5-Ind-araE/Plac-araBAD after 9 hours were 342 mM and 374 mM, respectively.

Further, under reducing conditions, *Corynebacterium glutamicum* X5-Ind-araE/Plac-araBAD was capable of simultaneous parallel utilization of three kinds of saccharides: D-glucose, D-xylose, and L-arabinose.

Example 8

Succinic Acid Production by *Corynebacterium glutamicum* R/pCRA811 and *Corynebacterium glutamicum* Ind-araE/pCRA811 Using Mixed Sugar of D-Glucose and D-Xylose as a Substrate Under Reducing Conditions

*Corynebacterium glutamicum* R/pCRA811 and *Corynebacterium glutamicum* Ind-araE/pCRA811 both prepared in the above Example 1 (5) were separately proliferated by aerobic culture in the same manner and under the same conditions as in the above Example 5, and then a succinic acid producing reaction was performed under reducing conditions.

As a result, the succinic acid production rates by *Corynebacterium glutamicum* R/pCRA811 and *Corynebacterium glutamicum* Ind-araE/pCRA811 at 3 hours after the start of the reaction were 14.2 mM/h and 16.9 mM/h, respectively.

Example 9

Construction of *Corynebacterium glutamicum* X5-Ind11-araE-Aldh/pEthAra (1) Method for Construction of Plasmid pEthAra A plasmid pCRA723 comprising 2 genes necessary for ethanol production: an aldehyde dehydrogenase gene (hereinafter referred to as adhB) and a pyruvate decarboxylase gene (hereinafter referred to as pdc) from *Zymomonas mobilis* (J. Mol. Microbiol. Biotechnol., Vol. 8, 243-254 (2004); and JP 2006-124440 A) was treated with restriction enzymes BamHI and BglII, and then the resultant fragments were separated by agarose gel electrophoresis. Then about 4.0-kb DNA fragments comprising an adhB-pdc gene from the gel were collected with use of MinElute Gel Extraction Kit (made by QIAGEN). The obtained DNA was blunt-ended with a blunting kit (trade name: DNA Blunting Kit, made by Takara Shuzo), and then mixed with the plasmid Plac-araBAD prepared in the above Example 6 (1), treated with the restriction enzyme SalI, and similarly blunt-ended. After addition of Mighty Cloning Kit (made by Takara Shuzo) thereto, the mixture was made to react according to the instruction manual.

With use of this ligation liquid, *Escherichia coli* JM109 was transformed by the calcium chloride method and was applied to L agar medium (the ingredient composition is the same as that of the above L medium except that L agar medium has 1.5% (w/v) of agar) containing 50 μg/mL of chloramphenicol.

Figure 10:
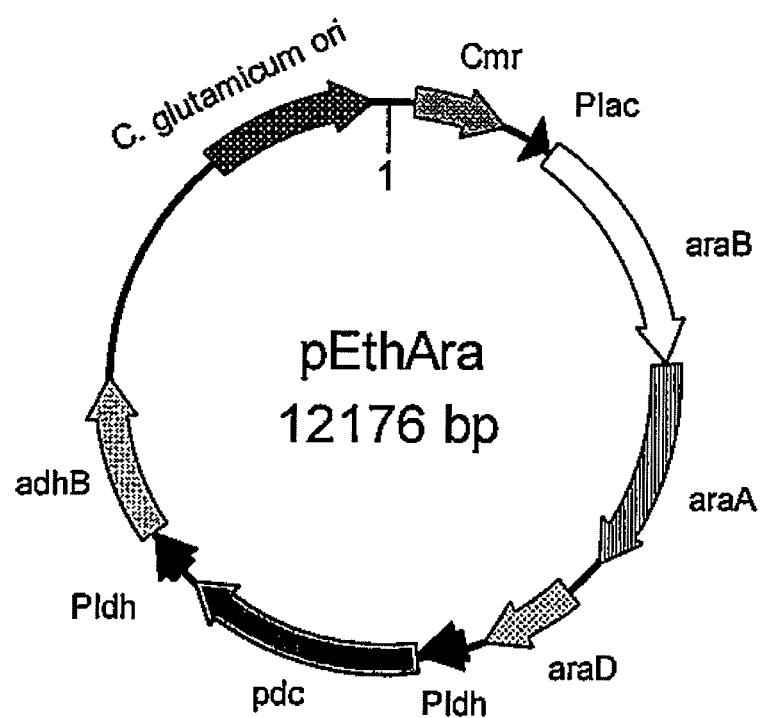
FIG. 10 is a schematic view showing the vector pEthAra prepared in Example 9.

A growing strain on the culture medium was subjected to liquid culture in the usual manner. A plasmid having an about 4.0-kb inserted DNA fragment comprising the adhB-pdc gene was extracted from the culture medium with use of QIAprep Spin Miniprep Kit (made by QIAGEN). The prepared plasmid was named pEthAra (FIG. 10).

(2) Preparation of *Corynebacterium glutamicum* X5-Ind-araE-Δldh

For markerless disruption of the lactate dehydrogenase (ldh) gene, pCRA728, a plasmid for markerless gene disruption (J. Mol. Microbiol. Biotechnol., Vol. 8, 243-254 (2004)), was transferred into *Corynebacterium glutamicum* X5-Ind11-araE according to the method mentioned in the above Example 1 (4). The finally obtained strain was named *Corynebacterium glutamicum* X5-Ind-araE-Δldh.

(3) Construction of *Corynebacterium glutamicum* X5-Ind-araE-Δldh/pEthAra

The plasmid pEthAra prepared in the above Example 9 (1) was transferred into *Corynebacterium glutamicum* X5-Ind-araE-Δldh according to the electric pulse method mentioned in the above Example 1 (4). With use of A agar medium (the ingredient composition is the same as that of the above A liquid medium except that A agar medium has 1.5% (w/v) of agar) containing 5 μg/mL of chloramphenicol, a transformed strain, that is, *Corynebacterium glutamicum* X5-Ind-araE-Δldh/pEthAra was obtained. *Corynebacterium glutamicum* X5-Ind-araE-Δldh/pEthAra was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-581 on Jun. 4, 2008.

Example 10

Sugar Consumption and Ethanol Production by *Corynebacterium glutamicum* X5-Ind-araE-Δldh/pEthAra Using Mixed Sugar of D-Glucose, D-Xylose, and L-Arabinose as a Substrate Under Reducing Conditions In the same manner and under the same conditions as in the above Example 3, *Corynebacterium glutamicum* X5-Ind-araE-Δldh/pEthAra was proliferated by aerobic culture. Then, the reaction under reducing conditions was performed in the same manner and under the same conditions as in the above Example 3 except that a mixture of D-glucose, D-xylose, and L-arabinose (32 g/L, 16 g/L, and 6.4 g/L, respectively; the ratio was 5:2.5:1) was used instead of D-xylose as the substrate.

Figure 11:
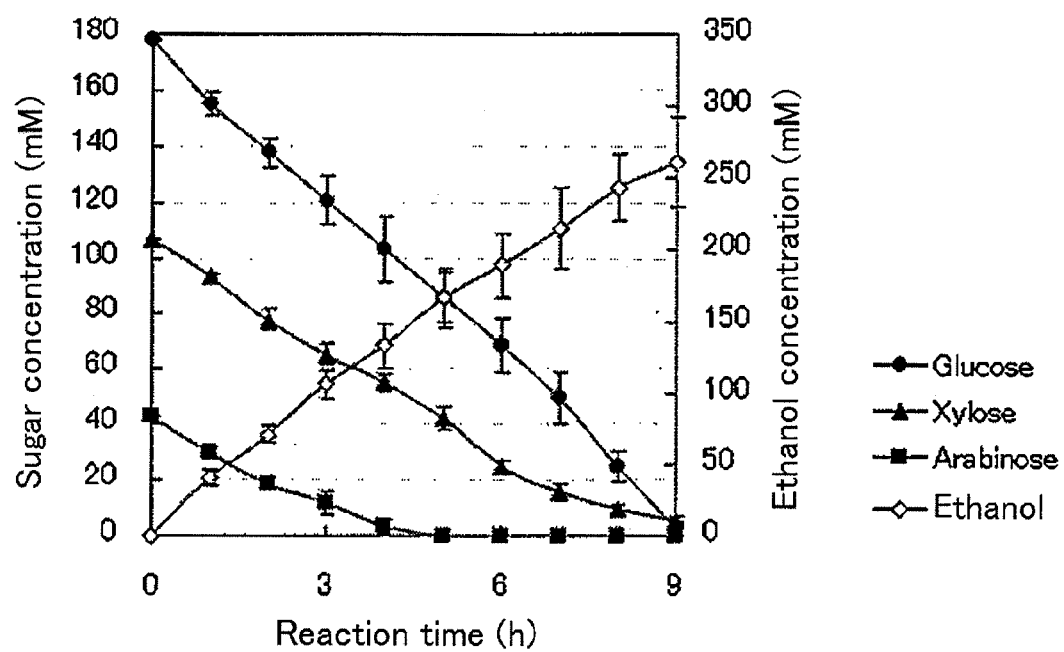
FIG. 11 shows the time course of sugar consumption and ethanol production by *Corynebacterium glutamicum* X5-Ind-araE-Δldh/pEthAra with use of mixed sugar of D-glucose, D-xylose, and L-arabinose (5:2.5:1).

As shown in FIG. 11, under reducing conditions, *Corynebacterium glutamicum* X5-Ind-araE-Δldh/pEthAra consumed the three kinds of saccharides: D-glucose, D-xylose, and L-arabinose in the culture medium within 9 hours, and produced ethanol. The consumption rates of the three kinds of saccharides in this case were almost equal to those of *Corynebacterium glutamicum* X5-Ind-araE/Plac-araBAD in Example 7. In FIG. 11, black circles show the change in the concentration of D-glucose in the culture medium. Triangles show the change in the concentration of D-xylose in the culture medium. Black rectangles show the change in the concentration of L-arabinose in the culture medium. White diamonds show the change in the concentration of ethanol in the culture medium.

Further, under reducing conditions, *Corynebacterium glutamicum* X5-Ind-araE-Δldh/pEthAra was capable of simultaneous parallel utilization of three kinds of saccharides: D-glucose, D-xylose, and L-arabinose.

INDUSTRIAL APPLICABILITY

The present invention can be preferably used for producing organic compounds from cellulosic biomass resources.

The invention claimed is:

1. A *Corynebacterium glutamicum* R transformed host cell prepared by transferring an exogenous gene comprising the sequence of SEQ ID NO: 13 encoding an L-arabinose transport system proton symporter, in an expression vector into the *Corynebacterium glutamicum* R having D-xylose-utilizing ability provided by an exogenous xylA gene and an exogenous xylB gene transferred into the *Corynebacterium glutamicum* R.

2. The *Corynebacterium glutamicum* R transformed host cell of claim 1, wherein the *Corynebacterium glutamicum* R is a strain having Accession Number FERM P-18976.

3. The *Corynebacterium glutamicum* R transformed host cell of claim 1, which is capable of simultaneous or parallel utilization of D-glucose and D-xylose.

4. The *Corynebacterium glutamicum* R transformed host cell of claim 3, which is capable of simultaneous or parallel utilization of D-glucose, D-xylose, and L-arabinose.

5. The *Corynebacterium glutamicum* R transformed host cell of claim 1, which is *Corynebacterium glutamicum* X5-Ind-araE/Plac-araBAD having Accession Number: NITE BP-577.

6. The *Corynebacterium glutamicum* R transformed host cell of claim 1, wherein the exogenous xylA gene and the exogenous xylB gene are isolated from *Escherichia coli*.

7. A method for producing an organic compound, which comprises a step of producing an organic compound with use of the coryneform bacterium transformant of claim 1 in a culture medium containing D-xylose, and a step of collecting the organic compound from the culture medium.

8. The method of claim 7, wherein the organic compound is at least one kind selected from the group consisting of ethanol, lactic acid, succinic acid, xylitol, acetic acid, and an amino acid.

* * * * *

SEQUENCE LISTING

<160> NUMBER OF SEQ ID NOS: 38

<210> SEQ ID NO 1
<211> LENGTH: 1323
<212> TYPE: DNA
<213> ORGANISM: Escherichia coli

<400> SEQUENCE: 1

```
atgcaagcct attttgacca gctcgatcgc gttcgttatg aaggctcaaa atcctcaaac      60
ccgttagcat tccgtcacta caatcccgac gaactggtgt tgggtaagcg tatggaagag     120
cacttgcgtt ttgccgcctg ctactggcac accttctgct ggaacggggc ggatatgttt     180
ggtgtggggg cgtttaatcg tccgtggcag cagcctggtg aggcactggc gttggcgaag     240
cgtaaagcag atgtcgcatt tgagttttc cacaagttac atgtgccatt ttattgcttc     300
cacgatgtgg atgtttcccc tgagggcgcg tcgttaaaag agtacatcaa taattttgcg     360
caaatggttg atgtcctggc aggcaagcaa gaagagagcg gcgtgaagct gctgtgggga     420
acggccaact gctttacaaa ccctcgctac ggcgcgggtg cggcgacgaa cccagatcct     480
gaagtcttca gctgggcggc aacgcaagtt gttacgcga tggaagcaac ccataaattg     540
ggcggtgaaa actatgtcct gtggggcggt cgtgaaggtt acgaaacgct gttaaatacc     600
```

| | |
|---|---|
| gacttgcgtc aggagcgtga caaactgggc cgctttatgc agatggtggt tgagcataaa | 660 |
| cataaaatcg gtttccaggg cacgttgctt atcgaaccga aaccgcaaga accgaccaaa | 720 |
| catcaatatg attacgatgc cgcgacggtc tatggcttcc tgaaacagtt tggtctggaa | 780 |
| aaagagatta aactgaacat tgaagctaac cacgcgacgc tggcaggtca ctctttccat | 840 |
| catgaaatag ccaccgccat tgcgcttggc ctgttcggtt ctgtcgacgc caaccgtggc | 900 |
| gatgcgcaac tgggctggga caccgaccag ttcccgaaca gtgtggaaga gaatgcgctg | 960 |
| gtgatgtatg aaattctcaa agcaggcggt ttcaccaccg tggtctgaa cttcgatgcc | 1020 |
| aaagtacgtc gtcaaagtac tgataaatat gatctgtttt acggtcatat cggcgcgatg | 1080 |
| gatacgatgg cactggcgct gaaaattgca gcgcgcatga ttgaagatgg cgagctggat | 1140 |
| aaacgcatcg cgcagcgtta ttccggctgg aatagcgaat tgggccagca aatcctgaaa | 1200 |
| ggccaaatgt cactggcaga tttagccaaa tatgctcagg aacatcattt gtctccggtg | 1260 |
| catcagagtg gtcgccagga caactggaa atctggtaa accattatct gttcgacaaa | 1320 |
| taa | 1323 |

<210> SEQ ID NO 2
<211> LENGTH: 1455
<212> TYPE: DNA
<213> ORGANISM: Escherichia coli
<400> SEQUENCE: 2

| | |
|---|---|
| atgtatatcg ggatagatct tggcaccctcg ggcgtaaaag ttattttgct caacgagcag | 60 |
| ggtgaggtgg ttgctgcgca aacggaaaag ctgaccgttt cgcgcccgca tccactctgg | 120 |
| tcggaacaag acccggaaca gtggtggcag gcaactgatc gcgcaatgaa agctctgggc | 180 |
| gatcagcatt ctctgcagga cgttaaagca ttgggtattg ccggcagat gcacggagca | 240 |
| accttgctgg atgctcagca acgggtgtta cgccctgcca ttttgtggaa cgacgggcgc | 300 |
| tgtgcgcaag agtgcacttt gctggaagcg cgagttccgc aatcgcgggt gattaccggc | 360 |
| aacctgatga tgcccggatt tactgcgcct aaattgctat gggttcagcg gcatgagccg | 420 |
| gagatattcc gtcaaatcga caaagtatta ttaccgaaag attacttgcg tctgcgtatg | 480 |
| acggggagt ttgccagcga tatgtctgac gcagctggca ccatgtggct ggatgtcgca | 540 |
| aagcgtgact ggagtgacgt catgctgcag gcttgcgact tatctcgtga ccagatgccc | 600 |
| gcattatacg aaggcagcga aattactggt gctttgttac ctgaagttgc gaaagcgtgg | 660 |
| ggtatggcga cggtgccagt tgtcgcaggc ggtggcgaca tgcagctgg tgcagttggt | 720 |
| gtgggaatgg ttgatgctaa tcaggcaatg ttatcgctgg ggacgtcggg ggtctatttt | 780 |
| gctgtcagcg aagggttctt aagcaagcca gaaagcgccg tacatagctt ttgccatgcg | 840 |
| ctaccgcaac gttggcattt aatgtctgtg atgctgagtg cagcgtcgtg tctggattgg | 900 |
| gccgcgaaat taaccggcct gagcaatgtc ccagctttaa tcgctgcagc tcaacaggct | 960 |
| gatgaaagtg ccgagccagt ttggtttctg ccttatcttt ccggcgagcg tacgccacac | 1020 |
| aataatcccc aggcgaaggg ggttttcttt ggtttgactc atcaacatgg ccccaatgaa | 1080 |
| ctggcgcgag cagtgctgga aggcgtgggt tatgcgctgg cagatggcat ggatgtcgtg | 1140 |
| catgcctgcg gtattaaacc gcaaagtgtt acgttgattg ggggcgggc gcgtagtgag | 1200 |
| tactggcgtc agatgctggc ggatatcagc ggtcagcagc tcgattaccg tacgggggg | 1260 |
| gatgtggggc cagcactggg cgcagcaagg ctggcgcaga tcgcggcgaa tccagagaaa | 1320 |
| tcgctcattg aattgttgcc gcaactaccg ttagaacagt cgcatctacc agatgcgcag | 1380 |

```
cgttatgccg cttatcagcc acgacgagaa acgttccgtc gcctctatca gcaacttctg    1440
ccattaatgg cgtaa                                                     1455
```

<210> SEQ ID NO 3
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 3

```
ctctgaattc acctgattat ggagttcaat                                     30
```

<210> SEQ ID NO 4
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 4

```
ctctcccggg catatcgatc gttccttaaa                                     30
```

<210> SEQ ID NO 5
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 5

```
ctctgaattc tttaaggaac gatcgatatg                                     30
```

<210> SEQ ID NO 6
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 6

```
ctctcccggg ttcagaataa attcatacta                                     30
```

<210> SEQ ID NO 7
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 7

```
ctctagatct ccgacatcat aacggttctg                                     30
```

<210> SEQ ID NO 8
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 8

```
ctctggatcc cttctctcat ccgccaaaac                                     30
```

<210> SEQ ID NO 9
<211> LENGTH: 30
<212> TYPE: DNA

<213> ORGANISM: Artificial Sequence
<220> FEATURE:
<223> OTHER INFORMATION: Synthetic construct; primer

<400> SEQUENCE: 9
ctctggatcc cttctctcat ccgccaaaac          30

<210> SEQ ID NO 10
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 10
ctcttgatca ccgacatcat aacggttctg          30

<210> SEQ ID NO 11
<211> LENGTH: 29
<212> TYPE: DNA
<213> ORGANISM: Artificial Sequence
<220> FEATURE:
<223> OTHER INFORMATION: Synthetic construct; primer
<220> FEATURE:
<221> NAME/KEY: misc_feature
<222> LOCATION: (3)..(3)
<223> OTHER INFORMATION: "n" stands for inosine
<220> FEATURE:
<221> NAME/KEY: misc_feature
<222> LOCATION: (9)..(9)
<223> OTHER INFORMATION: "n" stands for inosine
<220> FEATURE:
<221> NAME/KEY: misc_feature
<222> LOCATION: (15)..(15)
<223> OTHER INFORMATION: "n" stands for inosine
<220> FEATURE:
<221> NAME/KEY: misc_feature
<222> LOCATION: (16)..(16)
<223> OTHER INFORMATION: "n" stands for inosine
<220> FEATURE:
<221> NAME/KEY: misc_feature
<222> LOCATION: (18)..(18)
<223> OTHER INFORMATION: "n" stands for inosine
<220> FEATURE:
<221> NAME/KEY: misc_feature
<222> LOCATION: (21)..(21)
<223> OTHER INFORMATION: "n" stands for inosine
<220> FEATURE:
<221> NAME/KEY: misc_feature
<222> LOCATION: (24)..(24)
<223> OTHER INFORMATION: "n" stands for inosine
<220> FEATURE:
<221> NAME/KEY: misc_feature
<222> LOCATION: (27)..(27)
<223> OTHER INFORMATION: "n" stands for inosine

<400> SEQUENCE: 11
ggngayamna tgmgnnangt ngcngtnac          29

<210> SEQ ID NO 12
<211> LENGTH: 17
<212> TYPE: DNA
<213> ORGANISM: Artificial Sequence
<220> FEATURE:
<223> OTHER INFORMATION: Synthetic construct; primer
<220> FEATURE:
<221> NAME/KEY: misc_feature
<222> LOCATION: (12)..(12)
<223> OTHER INFORMATION: "n" stands for inosine

<400> SEQUENCE: 12
gtyttccart cnccytc          17

<210> SEQ ID NO 13
<211> LENGTH: 1720
<212> TYPE: DNA
<213> ORGANISM: Corynebacterium glutamicum 31831

<400> SEQUENCE: 13

```
gacagccggc caatcgaagg agtaatgatg acagagactg ttcaacaaac caagaagatc      60
ccccgaccgt acatctactt cttcggttca ttcggcggga ttctcttcgg ctacgacatc     120
ggcgtgatga ccggcgccct cccttctcta cagagtgact ggaacatcca gcacgaagcc     180
gccatcatcg gctggatcac ctcttcgctc atgcttggcg ccgtcttcgg cggtgtactc     240
gccggccagc tctccgacaa gctcggccgc cgcaaaatga tcctcttctc tgcgctggta     300
ttcatgatct tctcactcgg ctgcgcggtc gctccggacg gcggctgggt cttcctggcc     360
atcgtccgcg tgttcctcgg actcggcgtc ggcgcagcct ccgccctcgt ccccgcctac     420
atgtccgaaa tggcgcccgc gaagatccgc ggccggctct ccggcctcaa ccagacgatg     480
atcgtctccg gtatgctcgc ctcctacatt gtcgcttatt tcctgcgaaa cctccacgag     540
accaccgcat ggcggctcat gctcgggctc gccgcaatcc ctgccctcgt cctcttcctc     600
ggtgtgctgc gcctgccgga atcccgcgt ttcctcatca gaacggccg catcgaagag     660
gcccgcaccg tgctcagtta catccgcgat aacgacgcca tcgattccga gctcaagaac     720
atccaggaga ccgccgaact ggagaacgcc atccaggcca agaccagact cgcgacccta     780
ttcagcggac gctaccgcta cctcgtcgca gccggtgtcg gtgtcgctgc cttccagcag     840
ttccagggcg cgaacgccat cttctactac atcccgctca tcgtcgagaa ggcctccggc     900
accgaggcgt ccaatgcgct catgtggccg atcatccagg gcgtcatcct agttctcggt     960
tccctgctgt tcatggtcat cgccgacaag ttcaaccgac gcaccctgct cacagtcgga    1020
ggcacggtca tgggcctgtc tttcctcttc ccgaccttca ttcacatgac gatcccggat    1080
gccaacccca tgatgatcgt ggtcttcctg tccatctacg tggccttcta ctcctttacc    1140
tgggccccgc tgacctgggt catcgttggc gagatcttcc cgttagccat ccgcggccgc    1200
gcctccggat tggcgtcctc cttcaactgg atcggttcct tctccgtcgg cttactttc    1260
ccaattatga ccgcccagat gacccaggac gcggtcttcg cgatcttcgg catcatctgt    1320
atcctcggtg tcctgttcgt ccgattcctc gtcccagaga cccgcggacg cacactcgag    1380
gagattgagg ctcacggcac caaggccagg gtctgatacc tccgtcgcat cagcggagaa    1440
agcatcgccg cgtgcccggg gaatgtccga gatcgggcat ctgagtccac ccgcacgcat    1500
catcgatcac ctccctcct aagcgcctca cgacgccggg agacggggct gaacgttgac    1560
atggtcaagg aggaaccaac aacccgccga gtgctggtct ccgaaaacca gttaaaccca    1620
cgtaaccccg catacgcggg gttatcacgg cgcacagcac caacggcatc tctcaaaggg    1680
aatcccaact gtgctcttaa acactcctta gcctggattc                           1720
```

<210> SEQ ID NO 14
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 14

```
ctctgaattc cggccaatcg aaggagtaat                                        30
```

<210> SEQ ID NO 15

```
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 15
ctctgaattc aggctaagga gtgtttaaga                                    30

<210> SEQ ID NO 16
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 16
ctcttctaga cctcaataga gtcttcagat                                    30

<210> SEQ ID NO 17
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 17
ctcttctaga tgctcagtat gaatggcctt                                    30

<210> SEQ ID NO 18
<211> LENGTH: 4332
<212> TYPE: DNA
<213> ORGANISM: Escherichia coli

<400> SEQUENCE: 18
acccgttttt ttggatggag tgaaacgatg gcgattgcaa ttggcctcga ttttggcagt    60
gattctgtgc gagctttggc ggtggactgc gctaccggtg aagagatcgc caccagcgta   120
gagtggtatc cccgttggca gaaagggcaa ttttgtgatg ccccgaataa ccagttccgt   180
catcatccgc gtgactacat tgagtcaatg gaagcggcac tgaaaaccgt gcttgcagag   240
cttagcgtcg aacagcgcgc agctgtggtc gggattggcg ttgacagtac cggctcgacg   300
cccgcaccga ttgatgccga cggaaacgtg ctggcgctgc gcccggagtt tgccgaaaac   360
ccgaacgcga tgttcgtatt gtggaaagac cacactgcgg ttgaagaagc ggaagagatt   420
acccgtttgt gccacgcgcc gggcaacgtt gactactccc gctacattgg tggtatttat   480
tccagcgaat ggttctgggc aaaaatcctg catgtgactc gccaggacag cgccgtggcg   540
caatctgccg catcgtggat tgagctgtgc gactgggtgc agctctctgc ttccggtacc   600
acccgcccgc aggatattcg tcgcggacgt tgcagcgccg gcataaaatc tctgtggcac   660
gaaagctggg gcggcctgcc gccagccagt ttctttgatg agctggaccc gatcctcaat   720
cgccatttgc cttccccgct gttcactgac acttggactg ccgatattcc ggtgggcacc   780
ttatgcccgg aatgggcgca gcgtctcggc ctgcctgaaa gcgtggtgat ttccggcggc   840
gcgtttgact gccatatggg cgcagttggc gcaggcgcac agcctaacgc actggtaaaa   900
gttatcggta cttccacctg cgacattctg attgccgaca acagagcgt tggcgagcgg   960
gcagttaaag gtatttgcgg tcaggttgat ggcagcgtgg tgcctggatt tatcggtctg  1020
gaagcaggcc aatcgcgtt tggtgatatc tacgcctggt ttggtcgcgt actcggctgg  1080
ccgctggaac agcttgccgc ccagcatccg gaactgaaaa cgcaaatcaa cgccagccag  1140
```

```
aaacaactgc ttccggcgct gaccgaagca tgggccaaaa atccgtctct ggatcacctg   1200
ccggtggtgc tcgactggtt taacggccgc cgcacaccga acgctaacca acgcctgaaa   1260
ggggtgatta ccgatcttaa cctcgctacc gacgctccgc tgctgttcgg cggtttgatt   1320
gctgccaccg cctttggcgc acgcgcaatc atggagtgct ttaccgatca ggggatcgcc   1380
gttaataacg tgatggcact gggcggcatc gcgcggaaaa accaggtcat tatgcaggcc   1440
tgctgcgacg tgctgaatcg cccgctgcaa attgttgcct ctgaccagtg ctgtgcgctc   1500
ggtgcggcga ttttgctgc cgtcgccgcg aaagtgcacg cagacatccc atcagctcag   1560
caaaaaatgg ccagtgcggt agagaaaacc ctgcaaccgt gcagcgagca ggcacaacgc   1620
tttgaacagc tttatcgccg ctatcagcaa tgggcgatga gcgccgaaca acactatctt   1680
ccaacttccg ccccggcaca ggctgccag gccgttgcga ctctataagg acacgataat   1740
gacgattttt gataattatg aagtgtggtt tgtcattggc agccagcatc tgtatggccc   1800
ggaaaccctg cgtcaggtca cccaacatgc cgagcacgtc gttaatgcgc tgaatacgga   1860
agcgaaactg ccctgcaaac tggtgttgaa accgctgggc accacgccgg atgaaatcac   1920
cgctatttgc cgcgacgcga attacgacga tcgttgcgct ggtctggtgg tgtggctgca   1980
caccttctcc ccggccaaaa tgtggatcaa cggcctgacc atgctcaaca aaccgttgct   2040
gcaattccac acccagttca acgcggcgct gccgtgggac agtatcgata tggactttat   2100
gaacctgaac cagactgcac atggcggtcg cgagttcggc ttcattggcg cgcgtatgcg   2160
tcagcaacat gccgtggtta ccggtcactg gcaggataaa caagcccatg agcgtatcgg   2220
ctcctggatg cgtcaggcgg tctctaaaca ggatacccgt catctgaaag tctgccgatt   2280
tggcgataac atgcgtgaag tggcggtcac cgatggcgat aaagttgccg cacagatcaa   2340
gttcggtttc tccgtcaata cctgggcggt tggcgatctg gtgcaggtgg tgaactccat   2400
cagcgacggc gatgttaacg cgctggtcga tgagtacgaa agctgctaca ccatgacgcc   2460
tgccacacaa atccacggca aaaacgaca gaacgtgctg gaagcggcgc gtattgagct   2520
ggggatgaag cgtttcctgg aacaaggtgg cttccacgcg ttcaccacca cctttgaaga   2580
tttgcacggt ctgaaacagc ttcctggtct ggccgtacag cgtctgatgc agcagggtta   2640
cggctttgcg ggcgaaggcg actggaaaac tgccgccctg cttcgcatca tgaaggtgat   2700
gtcaaccggt ctgcagggcg gcacctcctt tatggaggac tacacctatc acttcgagaa   2760
aggtaatgac ctggtgctcg gctcccatat gctggaagtc tgcccgtcga tcgccgcaga   2820
agagaaaccg atcctcgacg ttcagcatct cggtattggt ggtaaggacg atcctgcccg   2880
cctgatcttc aatacccaaa ccggcccagc gattgtcgcc agcttgattg atctcggcga   2940
tcgttaccgt ctactggtta actgcatcga cacggtgaaa acaccgcact ccctgccgaa   3000
actgccggtg gcgaatgcgc tgtggaaagc gcaaccggat ctgccaactg cttccgaagc   3060
gtggatcctc gctggtggcg cgcaccatac cgtcttcagc catgcactga acctcaacga   3120
tatgcgccaa ttcgccgaga tgcacgacat tgaaatcacg gtgattgata acgacacacg   3180
cctgccagcg tttaaagacg cgctgcgctg gaacgaagtg tattacgggt tcgtcgcta   3240 agtagccgca tccggtatgt aacgcctgat gcgacgctga cgcgtcttat ctggcctaca   3300
cgctgcgatt ttgtaggccg gataagcaaa gcgcatccgg cattaacgc ctgatgcgac   3360 gctggcgcgt cttatcaggc ctacgcgctg cgattttgta ggccggataa gcaaagcgca   3420
tccggcattc aacgcctgat gcgacgctgg cgcgtcttat caggcctaca cgctgcgatt   3480
ttgtaggccg gataagcaaa gcgcatccgg cacgaaggag tcaacatgtt agaagatctc   3540
```

```
aaacgccagg tattagaagc caacctggcg ctgccaaaac acaacctggt cacgctcaca    3600
tggggcaacg tcagcgccgt tgatcgcgag cgcggcgtct ttgtgatcaa accttccggc    3660
gtcgattaca gcgtcatgac cgctgacgat atggtcgtgg ttagcatcga aaccggtgaa    3720
gtggttgaag gtacgaaaaa gccctcctcc gacacgccaa ctcaccggct gctctatcag    3780
gcattcccct ccattggcgg cattgtgcat acgcactcgc gccacgccac catctgggcg    3840
caggcgggtc agtcgattcc agcaaccggc accacccacg ccgactattt ctacggcacc    3900
attccctgca cccgcaaaat gaccgacgca gaaatcaacg gcgaatatga gtgggaaacc    3960
ggtaacgtca tcgtagaaac ctttgaaaaa cagggtatcg atgcagcgca aatgcccggc    4020
gttctggtcc attcccacgg cccgtttgca tggggcaaaa atgccgaaga tgcggtgcat    4080
aacgccatcg tgctggaaga ggtcgcttat atggggatat tctgccgtca gttagcgccg    4140
cagttaccgg atatgcagca aacgctgctg gataaacact atctgcgtaa gcatggcgcg    4200
aaggcatatt acgggcagta atgactgtat aaaaccacag ccaatcaaac gaaaccaggc    4260
tatactcaag cctggttttt tgatggattt tcagcgtggc gcaggcaggt tttatcttaa    4320
cccgacactg gc                                                       4332
```

<210> SEQ ID NO 19
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 19
ctctgaattc acccgttttt ttggatggag                                     30

<210> SEQ ID NO 20
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 20
ctctgtcgac gccagtgtcg ggttaagata                                     30

<210> SEQ ID NO 21
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 21
ctcttctaga tgatgaaggt ttccccgccg                                     30

<210> SEQ ID NO 22
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 22
ctcttctaga tcgtataccc ctatggggta                                     30

<210> SEQ ID NO 23
<211> LENGTH: 30
<212> TYPE: DNA

```
<213> ORGANISM: Artificial Sequence
<220> FEATURE:
<223> OTHER INFORMATION: Synthetic construct; primer

<400> SEQUENCE: 23
ctcttctaga gttccgcttc ggagagagat                                30

<210> SEQ ID NO 24
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 24
ctctgagctc caccgtcagg tgaaatacct                                30

<210> SEQ ID NO 25
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 25
ctctgagctc tgattgcacg atggcgaaaa                                30

<210> SEQ ID NO 26
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 26
ctctgtcgac ctgcaacaag tgaaaaaga                                 30

<210> SEQ ID NO 27
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 27
ctcttctaga gctgccgtag cttttttggga                               30

<210> SEQ ID NO 28
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 28
ctctctcgag tactcacctt ttcgatccgc                                30

<210> SEQ ID NO 29
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 29
ctctgagctc gtgaacatat cggcatcgag                                30
```

<210> SEQ ID NO 30
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 30
ctctgtcgac ctatggcgtt ctatactgcg                                    30

<210> SEQ ID NO 31
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 31
ctcttctaga tatgcaagaa gcaagcaagt                                    30

<210> SEQ ID NO 32
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 32
ctctctcgag tctcataaaa gttctccgat                                    30

<210> SEQ ID NO 33
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 33
ctctgagctc agctgagaga aaagctttcg                                    30

<210> SEQ ID NO 34
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 34
ctctgtcgac agagaccgta gagctaatcc                                    30

<210> SEQ ID NO 35
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 35
ctcttctaga gtctctaaac caaacaggtg                                    30

<210> SEQ ID NO 36
<211> LENGTH: 30
<212> TYPE: DNA
<213> ORGANISM: Artificial Sequence
<220> FEATURE:
<223> OTHER INFORMATION: Synthetic construct; primer

```
<400> SEQUENCE: 36
ctctctcgag aaccaccgaa tagcgcatgc                                    30

<210> SEQ ID NO 37
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 37
ctctgtcgac tccgtggaca attttcatcc                                    30

<210> SEQ ID NO 38
<211> LENGTH: 30
<212> TYPE: DNA
<213> ORGANISM: Artificial Sequence
<220> FEATURE:
<223> OTHER INFORMATION: Synthetic construct; primer

<400> SEQUENCE: 38
ctctgcatgc aagcacacca attagtaatg                                    30
```